US008551707B2

(12) United States Patent
Oeth et al.

(10) Patent No.: US 8,551,707 B2
(45) Date of Patent: Oct. 8, 2013

(54) NUCLEIC ACID-BASED TESTS FOR RHD TYPING, GENDER DETERMINATION AND NUCLEIC ACID QUANTIFICATION

(75) Inventors: Paul Andrew Oeth, San Diego, CA (US); Mathias Ehrich, San Diego, CA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 13/323,683

(22) Filed: Dec. 12, 2011

(65) Prior Publication Data

US 2012/0214680 A1 Aug. 23, 2012

Related U.S. Application Data

(63) Continuation of application No. 12/027,954, filed on Feb. 7, 2008, now Pat. No. 8,173,370.

(60) Provisional application No. 60/888,942, filed on Feb. 8, 2007.

(51) Int. Cl.
*C12Q 1/68* (2006.01)
*C12P 19/34* (2006.01)

(52) U.S. Cl.
USPC ........................ 435/6.12; 435/6.1; 435/6.11

(58) Field of Classification Search
None
See application file for complete search history.

(56) References Cited

U.S. PATENT DOCUMENTS

| | | | |
|---|---|---|---|
| 4,656,127 A | 4/1987 | Mundy |
| 4,683,195 A | 7/1987 | Mullis |
| 4,683,202 A | 7/1987 | Mullis |
| 4,851,331 A | 7/1989 | Vary |
| 4,965,188 A | 10/1990 | Mullis |
| 5,210,015 A | 5/1993 | Gelfand |
| 5,487,972 A | 1/1996 | Gelfand |
| 5,492,806 A | 2/1996 | Drmanac |
| 5,525,464 A | 6/1996 | Drmanac |
| 5,547,835 A | 8/1996 | Koster |
| 5,589,330 A | 12/1996 | Shuber |
| 5,605,798 A | 2/1997 | Koster |
| 5,656,493 A | 8/1997 | Mullis |
| 5,679,524 A | 10/1997 | Nikiforov |
| 5,691,141 A | 11/1997 | Koster |
| 5,695,940 A | 12/1997 | Drmanac |
| 5,723,293 A | 3/1998 | Huang |
| 5,834,189 A | 11/1998 | Stevens |
| 5,849,483 A | 12/1998 | Shuber |
| 5,849,542 A | 12/1998 | Reeve |
| 5,851,770 A | 12/1998 | Babon |
| 5,869,242 A | 2/1999 | Kamb |
| 5,876,934 A | 3/1999 | Duthie |
| 5,891,625 A | 4/1999 | Buchardt |
| 5,908,755 A | 6/1999 | Kumar |
| 5,912,118 A | 6/1999 | Ansorge |
| 5,928,906 A | 7/1999 | Koster |
| 5,952,174 A | 9/1999 | Nikiforov |
| 5,958,692 A | 9/1999 | Cotton |
| 5,976,802 A | 11/1999 | Ansorge |
| 5,981,186 A | 11/1999 | Gabe |
| 5,998,143 A | 12/1999 | Ellis |
| 6,004,744 A | 12/1999 | Goelet |
| 6,013,431 A | 1/2000 | Soderlund |
| 6,013,499 A | 1/2000 | Narumiya |
| 6,017,702 A | 1/2000 | Lee |
| 6,018,041 A | 1/2000 | Drmanac |
| 6,043,031 A | 3/2000 | Koster |
| 6,045,996 A | 4/2000 | Cronin |
| 6,046,005 A | 4/2000 | Ju |
| 6,087,095 A | 7/2000 | Rosenthal |
| 6,110,684 A | 8/2000 | Kemper |
| 6,136,541 A | 10/2000 | Gulati |
| 6,140,054 A | 10/2000 | Wittwer |
| 6,142,681 A | 11/2000 | Gulati |
| 6,156,501 A | 12/2000 | McGall |
| 6,183,958 B1 | 2/2001 | Stanton |
| 6,194,144 B1 | 2/2001 | Koster |
| 6,197,506 B1 | 3/2001 | Fodor |
| 6,210,891 B1 | 4/2001 | Nyren |
| 6,223,127 B1 | 4/2001 | Berno |
| 6,225,625 B1 | 5/2001 | Pirrung |
| 6,229,911 B1 | 5/2001 | Balaban |
| 6,239,273 B1 | 5/2001 | Pease |
| 6,258,538 B1 | 7/2001 | Koster |

(Continued)

FOREIGN PATENT DOCUMENTS

| | | |
|---|---|---|
| JP | 2004089057 | 3/2004 |
| JP | 2003513620 | 11/2005 |

(Continued)

OTHER PUBLICATIONS

Tate et al., "Genetic predictors of the maximum doses patients receive during clinical use of the anti-epileptic drugs carbamazepine and phenytoin," PNAS, Apr. 2005, vol. 102, No. 15, pp. 5507-5512.*
Avent et al., "Evidence of Genetic Diversity Underlying Rh D⁻, Weak D (Dᵘ), and Partial D Phenotypes as Determined by Multiplex Polymerase Chain Reaction Analysis of the RHD Gene," Blood, vol. 89, No. 7 Apr. 1, 1997: pp. 2568-2577.
Beiboer et al., "Rapid genotyping of blood group antigens by multiplex polymerase chain reaction and DNA microarray hybridization," Transfusion, May 2005, vol. 45, pp. 667-679.
Bischoff et al., "Nonvasive Determination of Fetal RhD Status Using Fetal DNA in Maternal Serum and PCR," J. Soc. Gynecol Invest. vol. 6. No. 2, Mar./Apr. 1999.
Buck et al., "Design Strategies and Performance of Custom DNA Sequencing Primers," Biotechniques, Sep. 1999, vol. 27, No. 3, pp. 528-536.
Chen & Kwok, "Template-directed dye-terminator incorporation (TDI) assay: a homogeneous DNA diagnostic method based on fluorescence resonance energy transfer," Nucleic Acids Research 25: 347-353 (1997).

(Continued)

*Primary Examiner* — Young J Kim
(74) *Attorney, Agent, or Firm* — Grant Anderson LLP

(57) ABSTRACT

The invention in part provides nucleic acid-based assays, which are particularly useful for non-invasive prenatal testing. The invention in part provides compositions and methods for RhD typing, detecting the presence of fetal nucleic in a sample, determining the relative amount of fetal nucleic acid in a sample and determining the sex of a fetus, wherein each of the assays may be performed alone or in combination.

2 Claims, 19 Drawing Sheets

(56) References Cited

U.S. PATENT DOCUMENTS

| | | | |
|---|---|---|---|
| 7,005,276 | B1 | 2/2006 | Flegel et al. |
| 7,252,949 | B2 | 8/2007 | Flegel et al. |
| 7,553,629 | B2 | 6/2009 | Flegel |
| 2005/0079521 | A1 | 4/2005 | Beaulieu |
| 2008/0261205 | A1 | 10/2008 | Denomme |
| 2008/0299562 | A1 | 12/2008 | Oeth et al. |
| 2009/0186340 | A1 | 7/2009 | Olsson et al. |
| 2010/0291572 | A1* | 11/2010 | Stoughton et al. ........... 435/6 |

FOREIGN PATENT DOCUMENTS

| | | |
|---|---|---|
| WO | WO 99/37763 | 7/1999 |
| WO | WO 00/52625 | 9/2000 |
| WO | WO 01/20039 | 3/2001 |
| WO | WO 01/25485 | 4/2001 |
| WO | WO 01/27326 | 4/2001 |
| WO | WO 01/27327 | 4/2001 |
| WO | WO 01/27329 | 4/2001 |
| WO | WO 01/29259 | 4/2001 |
| WO | WO 2006/032897 | 3/2006 |
| WO | WO 2008/009142 | 8/2008 |

OTHER PUBLICATIONS

Chen et al., "Fluorescence energy transfer detection as a homogeneous DNA diagnostic method," Proc. Natl. Acad. Sci. USA 94(20): 10756-10761 (1997).

Chow, et al., "Mass Spectrometric detection of a SNP panel as an internal positive control for fetal DNA analysis in maternal plasma," Clin. Chem. 53, 141-142 (2007).

Claussen et al., "Reliable test for prenatal prediction of fetal RhD type using maternal plasma from RhD negative women," Prenatal Diagnosis 2005:25: 1040-1044.

Costa et al., "Fetal RHD genotyping in maternal serum during the first trimester of pregnancy," British Journal of Hematology 2002, 119, 255-260.

Denomme et al., "High-throughput multiplex single-nucleotide polymorphism analysis for red cell and platelet antigen genotypes," Transfusion May 2005, vol. 45, pp. 660-666.

Ding Chunming et al., "MS analysis of single-nucleotide differences in circulating nucleic acids: Application to noninvasive prenatal diagnosis", PNAS, USA vol. 101, No. 29, Jul. 20, 2004, pp. 10762-10767.

Ekman et al., "Rh genotyping: avoiding false-negative and false-positive results among individuals of African ancestry," American Journal of Hematology, 2002, vo.. 69, pp. 34-40.

Faas et al., "Rh E/e genotyping by allele-specific primer amplification", Blood, vol. 85, No. 3, 1995, pp. 829-832.

Faas et al., "Detection of fetal RHD-specific sequences in maternal plasma," The Lancet, vol. 352, pp. 1196, Oct. 10, 1998.

Finning et al., "Prediction of fetal D status from maternal plasma:introduction of a new noninvasive fetal RHD genotyping service," Transfusion vol. 42, Aug. 2002 1079-1086.

Gautier et al., "Fetal RhD genotyping by maternal serum analysis: A two-year experience," American Journal of Obstetrics and Gynocology (2005) 192, 666-669.

Geifman-Holtzman et al., "Fetal RhD genotyping in fetal cells flow sorted from maternal blood," American Journal of Obstetrics and Gynecology, Mar. 1996, vol. 174, No. 3, pp. 818-822.

Genebank Accession No. AC093428, authors, Kaul et al., Jan. 2002, pp. 1-40.

Grompe et al., "Scanning detection of mutations in human ornithine transcarbamoylase by chemical mismatch cleavage," Proc. Natl. Acad. Sci. USA 86: 5885-5892 (1989).

Grompe, "The rapid detection of unknown mutations in nucleic acids," Nature Genetics 5: 111-117 (1993).

Harper et al., "Use of maternal plasma for noninvasive determination of fetal RhD status," American Journal of Obstetrics and Gynocology (2004) 191, 1730-1732.

Hoof et al., "PCR-Based RH genotyping with fetal DNA isolated using QIAamp Technology," Customer Application Article, pp. 19-21, Issue 4, 1999.

International Search Report and Written Opinion for International Application No. PCT/US08/53342, Date of Mailing Sep. 22, 2008.

Jurinke, C., et al., "MALDI-TOF mass spectrometry: a versatile tool for high-performance DNA analysis." Mol. Biotechnol. 26, 147-164 (2004).

Le Van Kim et al., "Molecular cloning and primary structure of the human blood group RhD polypeptide," PNAS vol. 89, pp. 10925-10929 Nov. 1992.

Le Van Kim et al., "Multiple Rh Messenger RNA Isoforms Are Produced by Alternative Splicing," Blood, vol. 80, No. 4 Aug. 15, 1992: pp. 1074-1078.

Li Ying et al. "Noninvasive genotyping fetal Kell blood group (KEL1) using cell-free fetal DNA in maternal plasma by MALDI-TOF mass spectrometry.", Prenatal Diagnosis Mar. 2008, vol. 28, No. 3, Feb. 4, 2008, pp. 203-208.

Li, Y., Wenzel, F., Holzgreve, W., Hahn, S., "Genotyping fetal paternally inherited SNPs by MALDI-TOF MS using cell-free fetal DNA in maternal plasma: Influence of size fractionation," Electrophoresis 27, 3889-3896 (2006).

Lo et al., "Presence of fetal DNA in maternal plasma and serum," Lancet 350, 485-487 (1997).

Lo et al., "Prenatal Diagnosis of Fetal RhD Status by Molecular Analysis of Maternal Plasma," The New England Journal of Medicine, vol. 339, No. 24, Dec. 10, 1998, pp. 1734-1738.

Lo, Y.M.D. et al. "Prenatal diagnosis of fetal RhD status by molecular analysis of maternal plasma," N. Engl. J. Med. 339, 1734-1738 (1998).

Lo, Y.M.D. et al. "Quantitative analysis of fetal DNA in maternal plasma and serum: implications for noninvasive prenatal diagnosis," Am. J. Hum. Genet. 62, 768-775 (1998).

Lo, Y.M.D., "Recent developments in fetal nucleic acids in maternal plasma: implications to noninvasive prenatal fetal blood group genotyping," Transfusion clinique et bilogique, 2006, vol. 13, pp. 50-52.

Moise, Kenneth J., "Fetal RhD typing with free DNA in maternal plasma," American Journal of Obstetrics and Gynecology (2005) 192, 663-665.

Oeth, P. et al., iPLEX# Assay: Increased Plexing Efficiency and Flexibility for MassARRAY® System through single base primer extension with mass-modified Terminators. SEQUENOM Application Note (2005).

Okuda et al., "The RhD Gene Is Highly Detectable in RhD-negative Japanese Donors," J. Clin. Invest., vol. 100, No. 2, Jul. 1997, 373-379.

Orita et al., "Detection of polymorphisms of human DNA by gel electrophoresis as single-strand conformation polymorphisms," Proc. Natl. Acad. Sci. U.S.A 86: 2766-2770 (1989).

Sheffield et al., "Identification of novel rhodopsin mutations associated with retinitis pigmentosa by GC-clamped denaturing gradient gel electrophoresis," Proc. Natl. Acad. Sci. USA 49: 699-706 (1991).

Simsek et al., "Rapid Rh D Genotyping by Polymerase Chain Reaction-Based Amplification of DNA," Blood, vol. 85, No. 10 May 15, 1995: pp. 2975-2980.

Singleton et al., "The presence of HHO Pseudogene containing a 37 Base Pair duplication and a nonsense mutation in Africans with the RH D-Negative Blood group phenotype," Blood, American Society of Hematology, USA, vol. 95, No. 1, Jan. 1, 2000, pp. 12-18.

Supplementary European Search Report dated: Jan. 11, 2011 in European Application No. EP08728318 filed on: Feb. 7, 2008 based on International Application No. PCT/US2008/053342 filed on: Feb. 7, 2008.

van der Schoot et al., "Prenatal typing of Rh and Kell blood group system antigens: the edge of a watershed.", Transfusion Medicine Reviews Jan. 2003, vol. 17, No. 1, Jan. 2003, pp. 31-44.

van der Schoot et al., "Non-invasive antenatal RHO typing", Transfusion Clinique et Biologique, Arnette-Blackwell, Paris, FR, vol. 13, No. 1-2, Mar. 1, 2006, pp. 53-57.

Van der Schoot, et al., "Real-time PCR of bi-allelic insertion/deletion polymorphisms can serve as a reliable positive control for cell-free fetal DNA in non-invasive prenatal genotyping," Blood 102, 93a (2003).

Van Kim et al., "Molecular Cloning and primary structure of the human blood group RhD polypeptide," Proc.Natl.Acad.Sci, 1992, vol. 89, pp. 10925-10929.

Wagner and Flegel, "RHD gene deletion occurred in Rhesus box," Blood, Jun. 15, 2000, vol. 95, No. 12, 3662-3668.

Wagner et al., "RHD positive haplotypes in D negative Europeans," BMC Genetics (2001) 2:10.

Wagner et al., Molecular Basis of Weak D Phenotypes, Blood, 1999, vol. 93, pp. 385-393.

White et al., "Detecting single base substitutions as heteroduplex polymorphisms," Genomics 12: 301-306 (1992).

Xiao Yan Zhong et al., "Risk free 1-4 simultaneous prenatal identification of fetal Rhesus D Status and sex by multiplex real-time PCR using cell free fetal DNA in maternal plasma", Swiss Medical Weekly, EMH Swiss Medical Publishers, Basel, CH, vol. 131, No. 5/06, Feb. 10, 2001, pp. 70-74.

Office Action mailed: Feb. 8, 2012 in U.S. Appl. No. 12/027,954, filed Feb. 7, 2008 and published as: US/2008/0299562 on: Dec. 4, 2005.

Office Action mailed: Jun. 24, 2011 in U.S. Appl. No. 12/027,954, filed Feb. 7, 2008 and published as: US/2008/0299562 on: Dec. 4, 2005.

Office Action mailed: Feb. 16, 2010 in U.S. Appl. No. 12/027,954, filed Feb. 7, 2008 and published as: US/2008/0299562 on: Dec. 4, 2005.

Office Action mailed: Mar. 20, 2009 in U.S. Appl. No. 12/027,954, filed Feb. 7, 2008 and published as: US/2008/0299562 on: Dec. 4, 2005.

Office Action mailed: Dec. 10, 2009 in U.S. Appl. No. 12/027,954, filed Feb. 7, 2008 and published as: US/2008/0299562 on: Dec. 4, 2005.

* cited by examiner

Exon 4:
Exon 4 and RhDΨ 37bp insertion detection
Amplicon 1:       108bp (functional RhD), 145bp (RhD pseudogene)
Forward Primer:   *ACGTTGGATG*GACTATCAGGGCTTGCCCCG
Reverse Primer:   *ACGTTGGATG*TGCGAACACGTAGATGTGCA
Extend Primer:    *C*TGCAGACAGACTACCACATGAAC
Extend Direction: F
RhD Call:         A
RhDΨ Call:        A & T
RhCE              C

```
seq1   GTAAGCTCTGAACACCAGTCTCATGGCTTCAAGTCACACCTCCTAAGTGAAGCTCTGAAC
       ||||||||||||||||||||||||| |||||||||||||||||||||||||||||||||
seq2   GTAAGCTCTGAACACCAGTCTCGTGGCTTCAAGTCACACCTCCTAAGTGAAGCTCTGAAC
       28600     28610     28620     28630     28640     28650

TTACTGGGTTTTATTGCAGACAGACTACCACATGAAC
```

```
seq1   TTTCTCCAAGGACTATCAGGGCTTGCCCC-GGGCAGAGGATGCCGACACTCACTGCTCTT
       ||||||||||| ||| |||||||| |||| ||||||||||||||||||||||||||||||
seq2   TTTCTCCAAGGACCATCAGGGCTTTCCCCTGGGCAGAGGATGCCGACACTCACTGCTCTT
       28660     28670     28680     28690     28700     28710 seq1   ACTGGGTTTTATTGCAGACAGACTACCACATGAACATGATGCACATCTACGTGTTCGCAG
       ||||||||||||||| |||||||||||||||||||  ||   ||||||||||||||||||
seq2   ACTGGGTTTTATTGCAGACAGACTACCACATGAACCTGAGGCACTTCTACGTGTTCGCAG
       28720     28730     28740     28750     28760     28770 seq1   CCTATTTTGGGCTGTCTGTGGCCTGGTGCCTGCCAAAGCCTCTACCCGAGGGAACGGAGG
       ||||| |||||||| ||||||||||||||||||||||||||||||||  |||||||||||
seq2   CCTATTTTGGGCTGACTGTGGCCTGGTGCCTGCCAAAGCCTCTACCCAAGGGAACGGAGG
       28780     28790     28800     28810     28820     28830 seq1   ATAAAGATCAGACAGCAACGATACCCAGTTTGTCTGCCATGCTGGGTAAGGACAAGGTGG
       ||||  |||||| |||||||||||||||||||||||||||||||||||||||||||||||
seq2   ATAATGATCAGAGAGCAACGATACCCAGTTTGTCTGCCATGCTGGGTAAGGACAAGGTGG
       28840     28850     28860     28870     28880     28890 seq1   GGTGAGTGGTCTCCTACTTGGGCTGAGCAGAATGGCTCAGAAAAGGCTCTGGCTGAAAAA
       |||||||||||||| |||||||||||||||||||||||||||||||||||||||||||||
seq2   GGTGAGTGGTCTCATACTTGGGCTGAGCAGAATGGCTCAGAAAAGGCTCTGGCTGAAAAA
       28900     28910     28920     28930     28940     28950
```

FIG.1A

Exon 4:
Zygosity of RhDΨ
Amplicon 1:       79bp
Forward Primer:   *ACGTTGGATG*AGAACGGAGGATAAAGATCAGAC
Reverse Primer:   *ACGTTGGATG*AGCCAGCATGGCAGACAAACTG
Extend Primer:    GATAAAGATCAGACAGCAAC
Extend Direction: F
RhDΨ Call:        A (homozygote); AG (heterozygote)
RhD and RhCE Call: G

```
seq1   GTAAGCTCTGAACACCAGTCTCATGGCTTCAAGTCACACCTCCTAAGTGAAGCTCTGAAC
       ||||||||||||||||||||||||| |||||||||||||||||||||||||||||||||
seq2   GTAAGCTCTGAACACCAGTCTCGTGGCTTCAAGTCACACCTCCTAAGTGAAGCTCTGAAC
       28600     28610     28620     28630     28640     28650 seq1   TTTCTCCAAGGACTATCAGGGCTTGCCCC-GGGCAGAGGATGCCGACACTCACTGCTCTT
       ||||||||||||| ||||||||| ||||| ||||||||||||||||||||||||||||
seq2   TTTCTCCAAGGACCATCAGGGCTTTCCCCTGGGCAGAGGATGCCGACACTCACTGCTCTT
       28660     28670     28680     28690     28700     28710 seq1   ACTGGGTTTTATTGCAGACAGACTACCACATGAACATGATGCACATCTACGTGTTCGCAG
       |||||||||||||||| ||||||||||||||||||| ||| ||| |||||||||||||
seq2   ACTGGGTTTTATTGCAGACAGACTACCACATGAACCTGAGGCACTTCTACGTGTTCGCAG
       28720     28730     28740     28750     28760     28770 seq1   CCTATTTTGGGCTGTCTGTGGCCTGGTGCCTGCCAAAGCCTCTACCCGAGGGAACGGAGG
       |||||||||||||| |||||||||||||||||||||||||||||||| |||||||||||
seq2   CCTATTTTGGGCTGACTGTGGCCTGGTGCCTGCCAAAGCCTCTACCCAAGGGAACGGAGG
       28780     28790     28800     28810     28820     28830

A(psi)
seq1   ATAAAGATCAGACAGCAACGATACCCAGTTTGTCTGCCATGCTGGGTAAGGACAAGGTGG
       |||| |||||||| ||||||  ||||||||||||||||||||||||||||||||||||
seq2   ATAATGATCAGAGAGCAACGATACCCAGTTTGTCTGCCATGCTGGGTAAGGACAAGGTGG
       28840     28850     28860     28870     28880     28890 seq1   GGTGAGTGGTCTCCTACTTGGGCTGAGCAGAATGGCTCAGAAAAGGCTCTGGCTGAAAAA
       ||||||||||||| ||||||||||||||||||||||||||||||||||||||||||||
seq2   GGTGAGTGGTCTCATACTTGGGCTGAGCAGAATGGCTCAGAAAAGGCTCTGGCTGAAAAA
       28900     28910     28920     28930     28940     28950
```

FIG. 1B

Exon 5:
Amplicon:         71bp
Forward Primer:   *ACGTTGGATG*AATCGAAAGGAAGAATGCCG
Reverse Primer:   *ACGTTGGATG*CTGAGATGGCTGTCACCACG
Extend Primer:    ATGCCGTGTTCAACACCTACTATGCT
Extend Direction: F
RhD Call:         G
RhCE Call:        C
Extend Primer:    GATGGCTGTCACCACGCTGACTGCTA
Extend Direction: R
RhD Call:         C
RhCE Call:        G

```
              28970     28980     28990     29000     29010     29020
seq1    TTTGGAGCAGGAGTGTGATTCTGGCCAACCACCCTCTCTGGCCCCCAGGCGCCCTCTTCT
        ||||||||||||||||||||||||||||||||||||||||||||||||||||||||||||
seq2    TTTGGAGCAGGAGTGTGATTCTGGCCAACCACCCTCTCTGGCCCCCAGGCGCCCTCTTCT
              29920     29930     29940     29950     29960     29970

29030     29040     29050     29060     29070     29080
seq1    TGTGGATGTTCTGGCCAAGTTTCAACTCTGCTCTGCTGAGAAGTCCAATCGAAAGGAAGA
        |||||||||||||||||||||| |||||||||||||||||||||||||||| ||||||||
seq2    TGTGGATGTTCTGGCCAAGTGTCAACTCTGCTCTGCTGAGAAGTCCAATCCAAAGGAAGA
              29980     29990     30000     30010     30020     30030

29090     29100     29110     29120     29130     29140
seq1    ATGCCGTGTTCAACACCTACTATGCTGTAGCAGTCAGCGTGGTGACAGCCATCTCAGGGT
        ||||| ||||||||||||||||||||| ||||||||||| ||||||||||||||||||||
seq2    ATGCCATGTTCAACACCTACTATGCTCTAGCAGTCAGTGTGGTGACAGCCATCTCAGGGT
              30040     30050     30060     30070     30080     30090

29150     29160     29170     29180     29190     29200
seq1    CATCCTTGGCTCACCCCCAAGGGAAGATCAGCAAGGTGAGCAGGGCGCTGCCCTTGGGCA
        |||||||||||||||||||| |||||||||||| ||||||||||||||||||||||||||
seq2    CATCCTTGGCTCACCCCCAAAGGAAGATCAGCATGGTGAGCAGGGCGCTGCCCTTGGGCA
              30100     30110     30120     30130     30140     30150
```

FIG.1C

Exon 6:
Amplicon:          83bp
Forward Primer:    *ACGTTGGATG*TGTGGCTGGGCTGATCT*G*CG
Reverse Primer:    *ACGTTGGATG*TTCAGCCAAAGCAGAGGAGG
Extend Primer:     AGTTGTCTAGTTTCTTACCGGCAGG
Extend Direction:  R
RhD Call:          A
RhCE Call:         G

```
             30770      30780      30790      30800      30810      30820
                                                                     G(psi)
seq1    GTGTTCTCTCTCTACCTTGCTTCCTTTACCCACACGCTATTTCTTTGCAGACTTATGTGC
        ||||||||||||||||||||||||||||||||||||||||||||||||||||||||||||
seq2    GTGTTCTCTCTCTACCTTGCTTCCTTTACCCACACGCTATTTCTTTGCAGACTTATGTGC
             31720      31730      31740      31750      31760      31770

30830      30840      30850      30860      30870      30880
seq1    ACAGTGCGGTGTTGGCAGGAGGCGTGGCTGTGGGTACCTCGTGTCACCTGATCCCTTCTC
        ||||||||||||||||||||||||||||||||||||||||||||||||||||||||||||
seq2    ACAGTGCGGTGTTGGCAGGAGGCGTGGCTGTGGGTACCTCGTGTCACCTGATCCCTTCTC
             31780      31790      31800      31810      31820      31830

30890      30900      30910      30920      30930      30940
seq1    CGTGGCTTGCCATGGTGCTGGGTCT TGTGGCTGGGCTGATCT CCG TCGGGGGAGCCAAGT
        ||||||||||||||||||||||||| ||||||||||||||||| | | ||||||||||||
seq2    CGTGGCTTGCCATGGTGCTGGGTCTTGTGGCTGGGCTGATCTCCATCGGGGGAGCCAAGT
             31840      31850      31860      31870      31880      31890

30950      30960      30970      30980      30990      31000
seq1    A CCTGCCGGTAAGAAACTAGACAACTAA CCTCCTCTGCTTTGGCTGAA GGCCAGCAGGAC
        | |||||||||||||||||||||||||||  |||||||||||||||||||||||||||||
seq2    G CCTGCCGGTAAGAAACTAGACAACTAATGCTCTCTGCTTTGGCTGAAGGCCAGCAGGAC
             31900      31910      31920      31930      31940      31950
```

FIG.1D

Exon 7:

| | |
|---|---|
| Amplicon: | 95 bp |
| Forward Primer: | *ACGTTGGATG*AGCTCCATCATGGGCTACAAC |
| Reverse Primer: | *ACGTTGGATG*TTGCCGGCTCCGACGGTATC |
| Extend Primer: | TGCTGGGTCTGCTTGGAGAGATCA |
| Extend Direction: | F |
| RhD Call: | T |
| RhCE Call: | C |

```
              34060      34070      34080      34090      34100      34110
seq1   TGCCAATCTGCTTATAATAACACTTGTCCACAGGGGTGTTGTAACCGAGTGCTGGGGATT
       |||||||||||||||||||||||||||||||||| |||||||||||||||||||||||||
seq2   TGCCAATCTGCTTATAATAACACTTGTCCACAGGTGTGTTGTAACCGAGTGCTGGGGATT
              35000      35010      35020      35030      35040      35050

34120      34130      34140      34150      34160      34170
seq1   CCCCACAGCTCCATCATGGGCTACAACTTCAGCTTGCTGGGTCTGCTTGGAGAGATCATC
       |  |||||  ||||  |||||| || || |||||||||||||||||||||||||||||| |
seq2   CACCACATCTCCGTCATGCACTCCATCTTCAGCTTGCTGGGTCTGCTTGGAGAGATCACC
              35060      35070      35080      35090      35100      35110

34180      34190      34200      34210      34220      34230
seq1   TACATTGTGCTGCTGGTGCTTGATACCGTCGGAGCCGGCAATGGCATGTGGGTCACTGGG
       |||||||||||||||||||||||  ||| |||  |   |||||||||||||||||||||
seq2   TACATTGTGCTGCTGGTGCTTCATACTGTCTGGAACGGCAATGGCATGTGGGTCACTGGG
              35120      35130      35140      35150      35160      35170

34240      34250      34260      34270      34280      34290
seq1   CTTACCCCCCATCCCCTTAACACTCCCCTCCAACTCAGGAAGAAATGTGTGCAGAGTCCT
       ||||||||||||||||||||||||||||||||||||||||||||||||||||||||||||
seq2   CTTACCCCCCATCCCCTTAACACTCCCCTCCAACTCAGGAAGAAATGTGTGCAGAGTCCT
              35180      35190      35200      35210      35220      35230
```

FIG.1E

RhD Exon 10:
Amplicon:           63bp
RhD Forward:        *ACGTTGGATG*ACGCTCATGACAGCAAAGTC
RhD Reverse Primer: *ACGTTGGATG*AACTCCATTTTCTCTGACTC
RhD Extend Primer:  GTCTCCAATGTTCGCGCAGGCAC
RhD Extend Direction: F
RhD Call:           T

```
56330     56340     56350     56360     56370     56380
seq1  AGATCAAGCCAAAATCAGTATGTGGGTTCATCTGCAATAAAAATGTTTGTTTTGCTTTTA
      ||||||||||||||||||||||||||||||||||||||||||||||||||||||||||||
seq2  AGATCAAGCCAAAATCAGTATGTGGGTTCATCTGCAATAAAAATGTTTGTTTTGCTTTTA
        58250     58260     58270     58280     58290     58300

56390     56400     56410     56420     56430     56440
seq1  CAGTTTCCTCATTTGGCTGTTGGATTTTAAGCAAAAGCATCCAAGAAAAACAAGGCCTGT
      ||||||||||||||||||||||||||||||||||||||||||||||||||||||||||||
seq2  CAGTTTCCTCATTTGGCTGTTGGATTTTAAGCAAAAGCATCCAAGAAAAACAAGGCCTGT
        58310     58320     58330     58340     58350     58360

56450     56460     56470     56480     56490     56500
seq1  TCAAAAACAAGACAACTTCCTCTCACTGTTGCCTGCATTTGTACGTGAGAAACGCTCATG
      ||||||||||||||||||||||||||||||||||||||||||||||||||||||||||||
seq2  TCAAAAACAAGACAACTTCCTCTCACTGTTGCCTGCATTTGTACGTGAGAAACGCTCATG
        58370     58380     58390     58400     58410     58420

56510     56520     56530     56540     56550     56560
seq1  ACAGCAAAGTCTCCAAT-GTTCGCGCAGGCACTGGAGTCAGAGAAAATGGAGTTGAATCCT
      ||||||||||||||||
seq2  ACAGCAAAGTCTCCTTATGTATAATGAAACAAGGTCAGAGACAGATTTGATA
```

FIG.1F

SRY

TTTCTAAAAGTCAAATGTTAGCCATCCTAGAAGTTGGGCATAAAATACTTGTAAGTATATGCTAATATTC
TGATACTTAATGCCTGTGAAAAATGTGTATAGAATTTTCAATTTTTAAATAGAAGTGAAGAAAAAGCGAT
AATAATTACTATAAATTCAATATGCAGTTATGTATGTATGTGTGTGGTTAAGACAATTAGGTTCTCATTA
AGCTTTGTTTTTTTAAAGATAACATACACATATATTGATAATGATAAACAATTCATATAGCTTTTTGTGT

SRY-3-h-i

CCTCTCGTTTTGTGACATAAAAGGTCAATGAAAAAATTGGCGATTAAGTCAAATT**CGCATTTTTCAGGAC
AGCAGTAGAGCAGTCAGGGAGGCAGATCAGCAGGGCAAGTAGTCAACGTTAC**TGAATTACCATGTTTTGC
TTGAGAATGAATACATTGTCAGGGTACTAGGGGGTAGGCTGGTTGGGCGGGGTTGAGGGGGTGTTGAGGG
CGGAGAAATGCAAGTTTCATTACAAAAGTTAACGTAACAAAGAATCTGGTAGAAGTGAGTTTTGGATAGT
AAAATAAGTTTCGAACTCTGGCACCTTTCAATTTTGTCGCACTCTCCTTGTTTTTGACAATGCAATCATA
TGCTTCTGCTATGTTAAGCGTATTCAACAGCGATGATTACAGTCCAGCTGTGCAAGAGAATATTCCCGCT
CTCCGGAGAAGCTCTTCCTTCCTTTGCACTGAAAGCTGTAACTCTAAGTATCAGTGTGAAACGGGAGAAA
ACAGTAAAGGCAACGTCCAGGATAGAGTGAAGCGACCCATGAACGCATTCATCGTGTGGTCTCGCGATCA

SRY-4-i

GAGGCGCAAGATGGCTCTAGAGAATCCCAGAATGCGAAACTCAGAGATCAGCAAGCAGCT**GGGATACCAG
TGGAAAATGC**TTACTGAAGCCGAAAAATGGCCATTCTTCCAGGAGGCACAGAAATTACAGGCCATGCACA
GAGAGAAATACCCGAATTATAAGTATCGACCTCGTCGGAAGGCGAAGATGCTGCCGAAGAATTGCAGTTT
GCTTCCCGCAGATCCCGCTTCGGTACTCTGCAGCGAAGTGCAACTGGACAACAGGTTGTACAGGGATGAC
TGTACGAAAGCCACACACTCAAGAATGGAGCACCAGCTAGGCCACTTACCGCCCATCAACGCAGCCAGCT

SRY-5-i

CACCGCAGCAACGGGACCGCTACAGCCACTGGACAAAGCTGTAGGACAATCGGGTAACATTGGCTA**CAAA
GACCTACCTAGATGCT**CCTTTTTACGATAACTTACAGCCCTCACTTTCTTATGTTTAGTTTCAATATTGT
TTTCTTTTCTCTGGCTAATAAAGGCCTTATTCATTTCAGTTTTACTGGTATTTCATTTTAAACTTAATTT
CAAGACAAGTTGTGTCAACACGATTAACATGCAAAGAAATAAGACATCCAGAAGTGAGCCTGCCTATGTT
TGTGGCCGTCAGAGTACTAACTTGATACAAACGGACACTGTGGCTTACTTTAAATGCTCTAATGAGAAAC
ACACTTGAAAATTGTACCAAAAAAAATCACACTTCTATATGCAGCGTGTTAAGCAGTCCTCTCTAGACCG
TGTATTCATTGGTCTTTCAGCTACTTTGTACGTGTCTATAAATTGCAGGTAACTAAGGAATGGATATGTA
AGCAGGATCAAACTTGTTTCTTTCTCTCCCCTTCACGCTGTGGAAAAAACCAGTTTTACCTCCACTTGCA
ATTCAGTTCCTTTACTCCATATAAATCCAAACGGTTGACATTTCCTTTCAACTAGTTATAAAATGCCTCT
GGTAAAACAAAATATTTAATTCCTTGTCATTTTTGTATCTCTATGAAACTTATCATTTTGCCTTTCTTCT
GAAAACTATCTTTTAAAATGGCAATCTACTTGTTTCCATGGCCTATTAACTTTTAAGCCTGTGGAATGAA

Forward PCR Primer
Reverse PCR Primer

FIG. 2

Extend Primer

SRY-3-h-i:

PCR-F: 5'- ACGTTGGATG CGCATTTTTCAGGACAGCAG-3'

PCR-R: 5'- ACGTTGGATG GTAACGTTGACTACTTGCCC-3'

Extend: 5'- CAGGACAGCAGTAGAGCA-3'

Competitor-S:
5'-CGCATTTTTCAGGACAGCAGTAGAGCACTCAGGGAGGCAGATCAGCAGGGCAAGTAGTCAACGTTAC-3'

Competitor-AS:
5'-GTAACGTTGACTACTTGCCCTGCTGATCTGCCTCCCTGAGTGCTCTACTGCTGTCCTGAAAAATGCG-3'

SRY-4-i:

PCR-F: 5'- ACGTTGGATG AGATGGCTCTAGAGAATCCC-3'

PCR-R: 5'- ACGTTGGATG GCATTTTCCACTGGTATCCC-3'

Extend: 5'- TCCCAGAATGCGAAACTC-3'

Competitor-S:
5'-
AGATGGCTCTAGAGAATCCCAGAATGCGAAACTCtGAGATCAGCAAGCAGCTGGGATACCAGTGGAAAATGC-3'

Competitor-AS:
5'-GCATTTTCCACTGGTATCCCAGCTGCTTGCTGATCTCaGAGTTTCGCATTCTGGGATTCTCTAGAGCCATCT-3'

SRY-5-i:

PCR-F: 5'- ACGTTGGATG AGCAACGGGACCGCTACAG-3'

PCR-R: 5'- ACGTTGGATG AGCATCTAGGTAGGTCTTTG-3'

Extend: 5'-(c)GTTACCCGATTGTCCTAC-3'

Note: non-templated c added for multiplex with Fetal Identifiers, not necessary if run with target gene panels alone.

Competitor-S:
5'-AGCAACGGGACCGCTACAGCCACTGGACAAAGCaGTAGGACAATCGGGTAACATTGGCTACAAAGACCTACCTAGATGCT-3'

Competitor-AS:
5'-AGCATCTAGGTAGGTCTTTGTAGCCAATGTTACCCGATTGTCCTACtGCTTTGTCCAGTGGCTGTAGCGGTCCCGTTGCT-3'

FIG.2(cont)

CDY

>chrY:26177118+26177212 95bp
>chrY:24603989-24604083 95bp

TCACGAGGTCAGGAGATCGAGACAATCCTGGCTAACATGGTGAAACCCCGTCTCTACTAAAAATACAACA
AATTCGTAGGGCCAGGTGGCAGGTG

| Amplification primer | Amplification primer | Extend Primer sequence |
|---|---|---|
| ACGTTGGATGAGGAGATCGAGACAATCCTG | ACGTTGGATGCTGGCCCTACGAATTTGTTG | cGGCCCTACGAATTTGTTGTATTTTT |

TTTY22

>chrY:6291654+6291734 81bp
>chrY:24603989-24604083 95bp

GCTACTTCTCTACCTTATGGCAGGGACTTGTCGCTAGGCAATGGTGGCATTCATTGTGATGCTAGCCAGA
GCTCACAGCTC

| Amplification primer | Amplification primer | Extend Primer |
|---|---|---|
| ACGTTGGATGTACCTTATGGCAGGGACTTG | ACGTTGGATGCTCTGGCTAGCATCACAATG | GGGACTTGTCGCTAGG |

FIG.2(cont)

Non-invasive prenatal sex test - AMG_(F/M)-

```
                    10         20         30         40         50         60
AM-X.SEQ    ACCTCATCCTGGGCACCCTGGTTATATCAACTTCAGCTATGAGGTAATTTTTCTCTTTAC
            X:::::::::::::::::::::::::::::::::::::::::::::::::::::::::::
AM-Y.SEQ    ACCTCATCCTGGGCACCCTGGTTATATCAACTTCAGCTATGAGGTAATTTTTCTCTTTAC
                    10         20         30         40         50         60

70         80         90        100        110        120
AM-X.SEQ    TAATTTTGACCATTGTTTGCGTTAACAATGCCCTGGGCTCTGTAAAGAATAGTGTGTTGA
            :::::::::: :: :::::::: ::: :: : ::::::::::::::::::::::: :: ::
AM-Y.SEQ    TAATTTTGATCACTGTTTGCATTAGCAGTCCCCTGGGCTCTGTAAAGAATAGTGGGTGGA
                    70         80         90        100        110        120

130        140        150        160        170
AM-X.SEQ    TTCTTTATCCCAGAT------GTTTCTCAAGTGGTCCTGATTTTACAGTTCCTACCACCA
            ::::: :::::X :: :::::::::::::::::  ::::::::::::::::::::::: ::
AM-Y.SEQ    TTCTTCATCCCAAATAAAGTGGTTTCTCAAGTGGTCCCAATTTTACAGTTCCTACCATCA
                   130        140        150        160        170        180

180        190        200        210
AM-X.SEQ    GCTTCCCAGTTTAAGCTCTGATGGTTGGCCTCAAGCCT
            ::::::::::::::::::::::::::::::::::::::
AM-Y.SEQ    GCTTCCCAGTTTAAGCTCTGATGGTTGGCCTCAAGCCT
                   190        200        210
```

Primers for non-invasive prenatal sex testing using AMG as target:

PCR primers:
AMG-F:    5'-ACGTTGGATGCCCTGGGCTCTGTAAAGAAT-3'
AMG-R:    5'-ACGTTGGATGAGGCTTGAGGCCAACCATCAG-3'

EXTEND primers:
AMG-E:    5'-TTCTTCATCCCAAATAAAGT-3'

Competitors:
AMG-X-S:
5'-CCCTGGGCTCTGTAAAGAATAGTGTGTTGATTCTTTATCCCAGAaGTTTCTCAAGTGGTCCTGATTTTACAGTTCCTACCACCA
GCTTCCCAGTTTAAGCTCTGATGGTTGGCCTCAAGCCT-3'

AMG-X-AS:
5'-AGGCTTGAGGCCAACCATCAGAGCTTAAACTGGGAAGCTGGTGGTAGGAACTGTAAAATCAGGACCACTTGAGAAACtTCTGGGATAAAGA
ATCAACACACTATTCTTTACAGAGCCCAGGG-3'

AMG-Y-S:
5'-CCCTGGGCTCTGTAAAGAATAGTGGGTGGATTCTTCATCCCAAATAAAGTcGTTTCTCAAGTGGTCCCAATTTTACAGTTCCTACCATCA
GCTTCCCAGTTTAAGCTCTGATGGTTGGCCTCAAGCCT-3'

AMG-Y-AS:
5'-AGGCTTGAGGCCAACCATCAGAGCTTAAACTGGGAAGCTGATGGTAGGAACTGTAAAATTGGGACCACTTGAGAAACgACTTTATTTGGGATGA
AGAATCCACCCACTATTCTTTACAGAGCCCAGGG

FIG.3A

Non-invasive prenatal sex test - AMG-XY-5-i

```
              10        20        30        40        50        60
AM-X.SEQ   ACCTCATCCTGGGCACCCTGGTTATATCAACTTCAGCTATGAGGTAATTTTTCTCTTTAC
           ::::::::::::::::::::::::::::::::::::::::::::::::::::::::::::
           X::
AM-Y.SEQ   ACCTCATCCTGGGCACCCTGGTTATATCAACTTCAGCTATGAGGTAATTTTTCTCTTTAC
              10        20        30        40        50        60

70        80        90       100       110       120
AM-X.SEQ   TAATTTTTGACCATTGTTTGCGTTAACAATGCCCTGGGCTCTGTAAAGAATAGTGTGTTGA
           :::::::: :: ::::::::: ::: :: :: :::::::::::::::::::::: :: ::
AM-Y.SEQ   TAATTTTTGATCACTGTTTGCATTAGCAGTCCCCTGGGCTCTGTAAAGAATAGTGGGTGGA
              70        80        90       100       110       120

130       140       150       160       170
AM-X.SEQ   TTCTTTATCCCAGAT------GTTTCTCAAGTGGTCCTGATTTTACAGTTCCTACCACCA
           ::::: ::::::X ::   :::::::::::::::  :::::::::::::::::::: ::
AM-Y.SEQ   TTCTTCATCCCAAATAAAGTGGTTTCTCAAGTGGTCCCAATTTTACAGTTCCTACCATCA
             130       140       150       160       170       180

180       190       200       210
AM-X.SEQ   GCTTCCCAGTTTAAGCTCTGATGGTTGGCCTCAAGCCT
           ::::::::::::::::::::::::::::::::::::::
AM-Y.SEQ   GCTTCCCAGTTTAAGCTCTGATGGTTGGCCTCAAGCCT
             190       200       210
```

Primers for non-invasive prenatal sex testing using AMG as target:

PCR primers:
AMG-XY-5-i-F:    5'-ACGTTGGATGTATCAACTTCAGCTATGAGG-3'
AMG-XY-5-i-R:    5'-ACGTTGGATGCACTATTCTTTACAGAGC-3'

EXTEND primers:
AMG-XY-5-i-E:    5'-CTTTACAGAGCCCAGGG-3'

Competitors:
AMG-XY-5-i-S:
5'-TATCAACTTCAGCTATGAGGTAATTTTTCTCTTTACTAATTTTGAYCAYTGTTTGCRTTARCARTaCCCTGGGCTCTGTAAAGAATAGTG-3'

AMG-XY-5-i-AS:
5'-CACTATTCTTTACAGAGCCCAGGGtARTGRTAARGCAAACAYTGYTCAAAATTAGTAAAGAGAAAAATTACCTCATAGCTGAAGTTGATA-3'

FIG.3B

Non-invasive prenatal sex test

```
                    10         20         30         40         50         60
AM-X.SEQ    ACCTCATCCTGGGCACCCTGGTTATATCAACTTCAGCTATGAGGTAATTTTTCTCTTTAC
            X:::::::::::::::::::::::::::::::::::::::::::::::::::::::::::
AM-Y.SEQ    ACCTCATCCTGGGCACCCTGGTTATATCAACTTCAGCTATGAGGTAATTTTTCTCTTTAC
                    10         20         30         40         50         60

70         80         90        100        110        120
AM-X.SEQ    TAATTTTGACCATTGTTTGCGTTAACAATGCCCTGGGCTCTGTAAAGAATAGTGTGTTGA
            :::::::::: :: ::::::: ::: :: : :::::::::::::::::::::: :: ::
AM-Y.SEQ    TAATTTTGATCACTGTTTGCATTAGCAGTCCCCTGGGCTCTGTAAAGAATAGTGGGTGGA
                    70         80         90        100        110        120

130        140        150        160        170
AM-X.SEQ    TTCTTTATCCCAGAT------GTTTCTCAAGTGGTCCTGATTTTACAGTTCCTACCACCA
            ::::: ::::::X ::     ::::::::::::::::: :: ::::::::::::: ::
AM-Y.SEQ    TTCTTCATCCCAAATAAAGTGGTTTCTCAAGTGGTCCCAATTTTACAGTTCCTACCATCA
                   130        140        150        160        170        180

180        190        200        210
AM-X.SEQ    GCTTCCCAGTTTAAGCTCTGATGGTTGGCCTCAAGCCT
            ::::::::::::::::::::::::::::::::::::::
AM-Y.SEQ    GCTTCCCAGTTTAAGCTCTGATGGTTGGCCTCAAGCCT
                   190        200        210
```

New primers for non-invasive prenatal sex testing using AMG as target:

PCR primers:
AMG-F:   5'-CCCTGGGCTCTGTAAAGAAT-3'
AMG-R:   5'-GAGCTTAAACTGGGAAGCTG-3'

EXTEND primers:
AMG-Y:   5'-TTCTTCATCCCAAATAAAGT-3'
AMG-CON: 5'-CCCTGGGCTCTGTAAAGAATAGT-3'

EXTEND products:
Y chromosome:      TTCTTCATCCCAAATAAAGTG
Template positive: CCCTGGGCTCTGTAAAGAATAGTG

RESULTS TABLE

| Sequence Name | Primer Sequence | No. of Nucleotides | Mass |
|---|---|---|---|
| AMG-Y primer | TTCTTCATCCCAAATAAAGT | 20 | 6011 |
| Ychromosome positive | TTCTTCATCCCAAATAAAGTg | 21 | 6340.2 |
| | | | |
| AMG-CON primer | CTGGGCTCTGTAAAGAATAGT | 21 | 6457.2 |
| template positive | CTGGGCTCTGTAAAGAATAGTg | 22 | 6786.4 |
| | | | |
| SRY primer | caggacagcagtagagca | 18 | 5550.6 |
| SRY extension product | caggacagcagtagagcag | 19 | 5879.8 |

FIG.3C

Non-invasive prenatal Albumin test

```
Query   1   GCTCAGTATCTTCAGCAGTGTCCATTTGAAGATCATGTAAAATTAGTGAATGAAGTAACT   60
            ||||||||||||||||||||||||||||||||||||||||||||||||||||||||||||
Sbjct 193   GCTCAGTATCTTCAGCAGTGTCCATTTGAAGATCATGTAAAATTAGTGAATGAAGTAACT
252

Query  61   GAATTTGC   68
            ||||||||
Sbjct 253   GAATTTGC   260
```

ALB Assay:

PCR-F: 5'-ACGTTGGATGCAGTATCTTCAGCAGTGTCC-3'

PCR-R: 5'-ACGTTGGATGGCAAATTCAGTTACTTCATTC-3'

Extend: 5'-CAGTGTCCATTTGAAGATC-3'

Competitor-S:
5'-CAGTATCTTCAGCAGTGTCCATTTGAAGATCtTGTAAAATTAGTGAATGAAGTAACTGAATTTGC-3'

Competitor-AS:
5'-GCAAATTCAGTTACTTCATTCACTAATTTTACAaGATCTTCAAATGGACACTGCTGAAGATACTG-3'

FIG.4

NUCLEIC ACID-BASED TESTS FOR RHD TYPING, GENDER DETERMINATION AND NUCLEIC ACID QUANTIFICATION

RELATED APPLICATIONS

This patent application is a continuation of U.S. patent application Ser. No. 12/027,954 filed on Feb. 7, 2008, entitled NUCLEIC ACID-BASED TESTS FOR RHD TYPING, GENDER DETERMINATION AND NUCLEIC ACID QUANTIFICATION, naming Paul Andrew Oeth, Mathias Ehrich, and Min Seob Lee as inventors, which claims the benefit of U.S. Provisional Patent Application No. 60/888,942 filed on Feb. 8, 2007, entitled NUCLEIC ACID-BASED TESTS FOR RHD TYPING, GENDER DETERMINATION AND NUCLEIC ACID QUANTIFICATION, naming Paul Andrew Oeth and Mathias Ehrich as inventors. The entirety of each of these patent applications is incorporated herein by reference, including, without limitation, all text, tables and drawings.

SEQUENCE LISTING

The instant application contains a Sequence Listing which has been submitted in ASCII format via EFS-Web and is hereby incorporated by reference in its entirety. Said ASCII copy, created on May 12, 2008, is named SEQ-6005-UT_Seqlist.txt and is 59,263 bytes in size.

FIELD

The invention pertains generally to the field of RhD typing, which finds use, for example, in prenatal testing.

BACKGROUND

The Rh system is a highly polymorphic blood group system that plays an important role in haemolytic transfusion reactions, neonatal haemolytic disease and autoimmune haemolytic anemia. There are two different, but highly homologous, genes in the Rh system. One gene (RhD) encodes the D polypeptide, while the other gene (RHCE) encodes the CcEe polypeptide. RhD carries the D antigen— the most potent blood group immunogen. This antigen is absent from a relatively large segment (15-17%) of the population (the Rh-negative phenotype), as a result of RhD gene deletion or other RhD gene alterations (e.g., gene conversion, Pseudogene RhD psi). As used herein the term "psi" refers to the Greek symbol "ψ." RHCE exists in four allelic forms and each allele determines the expression of two antigens in Ce, ce, cE or CE combination (RHCE is the collective name of the four alleles).

Tests for determining RhD type are critical for a wide range of applications. When blood of a rhesus D (RhD) positive donor is given to an RhD negative patient there is a high chance that alloantibody formation occurs. RhD antibodies will lead to rapid destruction of RhD-positive red cells and to transfusion reactions. Furthermore, when a woman with red cell or platelet antibodies becomes pregnant, those antibodies can cross the placenta and can destruct the red cells or the platelets of the unborn child.

In the past, nucleic acid-based RhD typing was performed on fetal nucleic acid procured through invasive means. However, conventional invasive sampling techniques that analyze fetal DNA from amniotic fluid or chorionic villus are costly and may lead to miscarriage and sensitization of the mother. An alternative source of fetal DNA was shown to be maternal plasma and serum (Lo et al., Lancet 350, 485-487 (1997)).

SUMMARY

Recent years have shown a significant increase in the efforts to use circulating cell-free fetal DNA in maternal plasma for non-invasive prenatal diagnostics for example in sex-linked disorders, fetal rhesus D status and beta-thalassaemia (Lo, Y. M. D. et al. Am. J. Hum. Genet. 62, 768-775 (1998); and Lo, Y. M. D. et al. N. Engl. J. Med. 339, 1734-1738 (1998); both of which are hereby incorporated by reference). In addition to prenatal diagnostics, circulating free fetal nucleic acid may also be used, inter alia, to determine the presence of fetal nucleic acid in a sample, to determine the amount of fetal nucleic acid in a sample, and to determine the sex of a fetus. A non-invasive RhD typing test that is sensitive and accurate enough to determine the RhD genotype of fetal DNA using maternal plasma, but also fast, reliable and affordable enough to be used for a wide range RhD-related applications (e.g., testing donor blood) can serve as an invaluable tool for prenatal diagnostics and blood-related testing.

The invention in part provides nucleic acid-based assays that are particularly useful for non-invasive prenatal testing. The invention in part provides compositions and methods for RhD typing, detecting the presence of fetal nucleic in a sample, determining the relative amount of fetal nucleic acid in a sample, and determining the sex of a fetus, wherein each of the assays may be performed alone or in combination.

The invention in part provides compositions and methods for determining RhD type. In one embodiment, the compositions and methods of the invention may be used to determine the presence or absence of one or more exons in the RhD gene. In a related embodiment, the compositions and methods of the invention may be used to determine the presence or absence of any one of exon 4, exon 5, exon 7 or exon 10 in the RhD gene. In a related embodiment, the compositions and methods of the invention may be used to determine the presence or absence of the RhD pseudogene psi. In a related embodiment, the zygosity of the pseudogene psi is also determined. In another related embodiment, the compositions and methods of the invention may be used to determine the presence or absence of exon 10 of the RhD gene, whereby the presence of exon 10 acts as a positive control for the occurrence of nucleic acid amplification. In another related embodiment, determining RhD type is carried out by annealing an extend primer to a region of the exon, and extending the primer with one or more nucleotides, chain terminating nucleotides or any combination thereof, further wherein the exon region is selected such that primer extension distinguishes between an RhD exon or RhC exon, and whereby the identity of the primer extension product confirms the presence of an RhD exon versus an RhC exon. In some embodiments, the exon region is selected such that primer extension distinguishes between an RhD exon or RhD pseudogene exon, and whereby the identity of the primer extension product confirms the presence of an RhD exon versus an RhD pseudogene exon. In a related embodiment, determining RhD type is carried out by annealing an extend primer to a region of the exon, and extending the primer with one or more nucleotides, chain terminating nucleotides or any combination thereof, further wherein the exon region is selected such that primer extension distinguishes between an RhD gene or RhD psi pseudogene, and whereby the identity of the primer extension product confirms the presence of an RhD gene versus an RhD psi pseudogene.

In certain embodiments, a probe oligonucleotide having the nucleotide sequence of an extend primer described herein, or a nucleotide sequence that is about 90% or more identical (e.g., about 90%, 91%, 92%, 93%, 94%, 95%, 96%, 97%, 98% or 99% or more identical) to the sequence of an extend primer, and further wherein the primer still is specific for a given Rh exon (i.e., specifically hybridizes to a Rh exon) is utilized in place of an extend primer. In such embodiments, the probe oligonucleotide includes a quenchable, detectable label, such as a fluorescent label suitable for use in quantitative polymerase chain reaction detection procedures, for example, known to the person of ordinary skill in the art. Such probe oligonucleotides can be utilized in detection procedures known to the person of ordinary skill in the art, such as quantitative polymerase chain reaction procedures (utilized in a quantitative or non-quantitative format). Quantitative polymerase chain reaction procedures often incorporate the use of a polymerase having exonuclease activity selected by the person of ordinary skill in the art.

The invention in part provides compositions and methods to analyze a nucleic acid sample for the presence or absence of one or more RhD exons, comprising the steps of amplifying the one or more RhD exons with one or more primer pairs provided in Table 3; determining the presence or absence of the amplification products from the amplification reaction, thereby determining the Rh status of an individual. In a related embodiment, the sample is blood from a pregnant female. In some embodiments, one or more of exon 4, exon 5, exon 7 or exon 10 of the RhD gene. In some embodiments, one or more of exon 4, exon 5, exon 7 or exon 10 of the RHCE gene is analyzed. In some embodiments, the exons are analyzed in a multiplexed amplification reaction. In a related embodiment, two or more multiplexed assays are performed in parallel. In some embodiments, the sample is blood, plasma or serum from a pregnant female. In a related embodiment, the sample contains fetal nucleic acid and maternal nucleic acid. In a related embodiment, the RhD status of the fetus and mother are determined in a multiplexed amplification reaction, or a combination of two or more multiplexed reactions. In a related embodiment, the primer pairs in Table 3 comprise a tag sequence to improve multiplexing. In some embodiments, the presence or absence of amplification products is determined by mass spectrometry. In some embodiments, the presence or absence of amplification products is determined by detection of hybridization of the amplification products to a gene chip. In some embodiments, the presence or absence of amplification products is determined by real time-PCR (alternatively called RT-PCR or Q-PCR).

In a related embodiment, the invention in part provides a method of analyzing a sample comprising nucleic acid to determine an Rh genotype, comprising amplifying one or more RhD gene exons or fragments thereof with one or more pairs, or combinations thereof, of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

```
Exon 4 (psi zygosity) Primer Pair 1:
ACGTTGGATGCTGCCAAAGCCTCTACACG          (SEQ ID NO: 1)
and ACGTTGGATGTGGCAGACAAACTGGGTGTC;        (SEQ ID NO: 2)
or Exon 4 (psi zygosity) Primer Pair 2:
ACGTTGGATGAGAACGGAGGATAAAGATCAGAC      (SEQ ID NO: 3)
and

ACGTTGGATGAGCCAGCATGGCAGACAAACTG,      (SEQ ID NO: 4)
``` and analyzing the amplification products from the first step to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag nucleotide sequence may be any tag sequence known in the art, or selected by a person of ordinary skill in the art, that improves multiplexing (e.g., improves mass spectrometry multiplexing). In some embodiments, the invention in part includes primers that are substantially similar to the primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon). For example, one or more bases of a primer sequence may be changed or substituted, for example with an inosine, but the primer still maintains the same specificity and plexing ability.

In a related embodiment, the invention in part provides a method of analyzing a sample comprising nucleic acid to determine an Rh genotype, comprising amplifying one or more RhD gene exons or fragments thereof with one or more pairs, or combinations thereof, of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

```
Exon 4 (psi insertion) Primer Pair 1:
ACGTTGGATGGACTATCAGGGCTTGCCCCG         (SEQ ID NO: 5)
and

ACGTTGGATGTGCGAACACGTAGATGTGCA;        (SEQ ID NO: 6)
``` and analyzing the amplification products from the first step to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that improves multiplexing (e.g., multiplex analysis by mass spectrometry). In some embodiments, the invention in part includes primers that are substantially similar to the primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon).

In a related embodiment, the invention in part provides a method of analyzing a sample comprising nucleic acid to determine an Rh genotype, comprising amplifying one or more RhD gene exons or fragments thereof with one or more pairs, or combinations thereof, of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

```
Exon 7 Primer Pair 1:
                                (SEQ ID NO: 7)
ACGTTGGATGAATCGAAAGGAAGAATGCCG
and (SEQ ID NO: 8)
ACGTTGGATGCTGAGATGGCTGTCACCACG;
``` and analyzing the amplification products from the first step to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that improves multiplexing (e.g., multiplex analysis by mass spectrometry). In some embodiments, the invention in part includes primers that are substantially similar to the primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon).

In a related embodiment, the invention in part provides a method of analyzing a sample comprising nucleic acid to determine an Rh genotype, comprising amplifying one or more RhD gene exons or fragments thereof with one or more pairs, or combinations thereof, of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

```
Exon 7 Primer Pair 1:
                                (SEQ ID NO: 9)
ACGTTGGATGAGCTCCATCATGGGCTACAA
and (SEQ ID NO: 10)
ACGTTGGATGTTGCCGGCTCCGACGGTATC;
or Exon 7 Primer Pair 2:
                                (SEQ ID NO: 11)
ACGTTGGATGAGCTCCATCATGGGCTACAAC
and (SEQ ID NO: 10)
ACGTTGGATGTTGCCGGCTCCGACGGTATC,
``` and analyzing the amplification products from the first step to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that improves multiplexing (e.g., multiplex analysis by mass spectrometry). In some embodiments, the invention in part includes primers that are substantially similar to the primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon).

In a related embodiment, the invention in part provides a method of analyzing a sample comprising nucleic acid to determine an Rh genotype, comprising amplifying one or more RhD gene exons or fragments thereof with one or more pairs, or combinations thereof, of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

```
                                (SEQ ID NO: 12)
ACGTTGGATGACGCTCATGACAGCAAAGTC
and (SEQ ID NO: 13)
ACGTTGGATGAACTCCATTTTCTCTGACTC;

Exon 10 Primer Pair 2:
                                (SEQ ID NO: 14)
ACGTTGGATGACTCCATTTTCTCTGACTC
and (SEQ ID NO: 12)
ACGTTGGATGACGCTCATGACAGCAAAGTC,
``` and analyzing the amplification products from the first step to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that improves multiplexing (e.g., multiplex analysis by mass spectrometry). In some embodiments, the invention in part includes primers that are substantially similar to the primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon).

Primer Extension

The invention in part provides compositions and methods to analyze a nucleic acid sample for the presence of one or more RhD exons, comprising the steps of amplifying the one or more RhD exons with one or more primer pairs provided in Table 3; annealing one or more extend primers to the amplification products of first step, the extend primers provided in Table 3; performing a primer extension reaction; and analyzing the primer extension products to determine the Rh status of a fetus. The primer extension products may be analyzed using the RhD Test Interpretation Table provided in Table 1. In some embodiments, the presence or absence of primer extension products is determined by mass spectrometry. In some embodiments, the presence or absence of primer extension products is determined by any method known in the art.

In a related embodiment, the invention in part provides a method of analyzing a sample comprising nucleic acid to determine an Rh genotype, comprising the steps of amplifying one or more RhD gene exons or fragments thereof with one or more pairs of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

```
                                            (SEQ ID NO: 1)
ACGTTGGATGCTGCCAAAGCCTCTACACG
and
                                            (SEQ ID NO: 2)
ACGTTGGATGTGGCAGACAAACTGGGTGTC;
or Exon 4 (psi zygosity) Primer Pair 2:
                                            (SEQ ID NO: 3)
ACGTTGGATGAGAACGGAGGATAAAGATCAGAC
and
                                            (SEQ ID NO: 4)
ACGTTGGATGAGCCAGCATGGCAGACAAACTG;
``` annealing one or more extend primers to the amplification products from the first step, the extend primer comprising:

```
                                           (SEQ ID NO: 15)
gGTCTCCAATGTTCGCGCAGGCAC,
or
                                           (SEQ ID NO: 16)
gGATAAAGATCAGACAGCAAC;
``` extending the primer with one or more nucleotides; and analyzing the primer extension products to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that improves multiplexing (e.g., multiplex analysis by mass spectrometry). In some embodiments, the invention in part includes primers that are substantially similar to the amplification and extend primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon). For example, one or more bases of a primer sequence may be changed or substituted, for example with an inosine, but the primer still maintains the same specificity and plexing ability.

In a related embodiment, the invention in part provides a method of analyzing a sample comprising nucleic acid to determine an Rh genotype, comprising the steps of amplifying one or more RhD gene exons or fragments thereof with one or more pairs of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

```
                                            (SEQ ID NO: 5)
ACGTTGGATGGACTATCAGGGCTTGCCCCG
and
                                            (SEQ ID NO: 6)
ACGTTGGATGTGCGAACACGTAGATGTGCA;
``` annealing one or more extend primers to the amplification products from the first step, the extend primer comprising:

```
                                           (SEQ ID NO: 17)
GAACGGAGGATAAAGATCAGA,
or
                                           (SEQ ID NO: 18)
cTGCAGACAGACTACCACATGAAC;
``` extending the primer with one or more nucleotides; and analyzing the primer extension products to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that improves multiplexing (e.g., multiplex analysis by mass spectrometry). In some embodiments, the invention in part includes primers that are substantially similar to the amplification and extend primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon).

In a related embodiment, the invention in part provides a method of analyzing a sample comprising nucleic acid to determine an Rh genotype, comprising the steps of amplifying one or more RhD gene exons or fragments thereof with one or more pairs of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

```
                                            (SEQ ID NO: 7)
ACGTTGGATGAATCGAAAGGAAGAATGCCG
and
                                            (SEQ ID NO: 8)
ACGTTGGATGCTGAGATGGCTGTCACCACG;
``` annealing one or more extend primers to the amplification products from the first step, the extend primer comprising:

```
                                            (SEQ ID NO: 19)
ATGCCGTGTTCAACACCTACTATGCT, (SEQ ID NO: 20)
GATGGCTGTCACCACGCTGACTGCTA,
or (SEQ ID NO: 21)
tTGTCACCACGCTGACTGCTA;
``` extending the primer with one or more nucleotides; and analyzing the primer extension products to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that improves multiplexing (e.g., multiplex analysis by mass spectrometry). In some embodiments, the invention in part includes primers that are substantially similar to the amplification and extend primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon).

In a related embodiment, the invention in part provides a method of analyzing a sample comprising nucleic acid to determine an Rh genotype, comprising the steps of amplifying one or more RhD gene exons or fragments thereof with one or more pairs of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

```
                                            (SEQ ID NO: 9)
ACGTTGGATGAGCTCCATCATGGGCTACAA
and (SEQ ID NO: 10)
ACGTTGGATGTTGCCGGCTCCGACGGTATC;
or Exon 7 Primer Pair 2:
                                            (SEQ ID NO: 11)
ACGTTGGATGAGCTCCATCATGGGCTACAAC
and (SEQ ID NO: 12)
ACGTTGGATGTTGCCGGCTCCGACGGTATC;
``` annealing one or more extend primers to the amplification products from the first step, the extend primer comprising:

```
                                            (SEQ ID NO: 22)
CTTGCTGGGTCTGCTTGGAGAGATCA;
``` extending the primer with one or more nucleotides; and analyzing the primer extension products to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that improves multiplexing (e.g., multiplex analysis by mass spectrometry). In some embodiments, the invention in part includes primers that are substantially similar to the amplification and extend primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon).

In a related embodiment, the invention in part provides a method of analyzing a sample comprising nucleic acid to determine an Rh genotype, comprising the steps of amplifying one or more RhD gene exons or fragments thereof with one or more pairs of amplification primers (i) comprising one of the full length nucleotide sequences hereafter, (ii) comprising one of the underlined nucleotide sequences hereafter, or (iii) comprising one of the underlined nucleotide sequences hereafter and a tag nucleotide sequence:

```
                                            (SEQ ID NO: 12)
ACGTTGGATGACGCTCATGACAGCAAAGTC
and (SEQ ID NO: 13)
ACGTTGGATGAACTCCATTTTCTCTGACTC;

Exon 10 Primer Pair 2:
                                            (SEQ ID NO: 14)
ACGTTGGATGACTCCATTTTCTCTGACTC
and (SEQ ID NO: 12)
ACGTTGGATGACGCTCATGACAGCAAAGTC;
``` annealing one or more extend primers to the amplification products from the first step, the extend primer comprising:

```
                                            (SEQ ID NO: 15)
gGTCTCCAATGTTCGCGCAGGCAC;
``` extending the primer with one or more nucleotides; and analyzing the primer extension products to determine the presence or absence of one or more RhD gene exons or fragments thereof, wherein the presence or absence of one or more RhD gene exons or fragments thereof is indicative of an Rh genotype. In some embodiments, each primer of the amplification primer pair may comprise the entire sequence shown or only the underlined sequence, wherein the underlined portion of the primer is a sequence-specific primer sequence and the non-underlined portion is a tag sequence for improved multiplexing. The tag sequence may be any tag sequence known in the art that enables multiplexing. In some embodiments, the invention in part includes primers that are substantially similar to the amplification and extend primers provided herein, for example, a primer having a nucleotide sequence that is about 90% or more identical (e.g., about 90%, 91%, 92%, 93%, 94%, 95%, 96%, 97%, 98% or 99% or more identical), and further wherein the primer still is specific for a given Rh exon (i.e., specifically hybridizes to a Rh exon).

In another related embodiment, the invention in part provides a method of analyzing a sample derived from a pregnant female for the presence of one or more of exon 4, exon 5, exon 7 or exon 10 of the RhD gene from fetal nucleic acid, and exon 10 of the RhD gene from maternal nucleic acid, comprising the steps of amplifying the RhD nucleic acid with one or more primer pairs provided in Table 3; determining the presence or absence of the amplification products from the first step, thereby determining the Rh status of a fetus. In an optional embodiment, the presence or absence of exon 10 of the RhD gene may serve as a positive control for the occurrence of nucleic acid amplification or a primer extension reaction. In another related embodiment, a primer extension reaction is performed to determine the presence or absence of one or more of exon 4, exon 5, exon 7 or exon 10 of the RhD gene from fetal nucleic acid, and exon 10 of the RhD gene from maternal nucleic acid, wherein the extend primers are provided in Table 3.

The amplification products and/or primer extension products may be detected by any detection method known in the art, which includes but is not limited to RT-PCR, mass spectrometry and hybridization to a gene chip.

In one embodiment, the primer extension reaction includes the incorporation of a chain terminating nucleotide. In a related embodiment, the chain terminating nucleotide is a dideoxynucleotide, dideoxybromouridine or acyclonucleotide. In some embodiments, the extension reaction comprises incorporation of a deoxynucleotide, a dideoxynucleotide or a combination thereof. In some embodiments, the extension reaction comprises incorporation of a labeled nucleotide. In a related embodiment, the extension reaction comprises using a mixture of labeled and unlabeled nucleotides. In another related embodiment, the labeled nucleotide is labeled with a molecule selected from the group consisting of radioactive molecule, fluorescent molecule, mass label, antibody, antibody fragment, hapten, carbohydrate, biotin, derivative of biotin, phosphorescent moiety, luminescent moiety, electrochemiluminescent moiety, chromatic moiety, and moiety having a detectable electron spin resonance, electrical capacitance, dielectric constant and electrical conductivity. In another related embodiment, the labeled nucleotide is labeled with a fluorescent molecule.

The invention in part provides compositions and methods to detect the presence or absence of a target nucleic acid in a sample. In one embodiment, the compositions and methods of the invention may be used to detect the presence or absence of fetal nucleic acid in a maternal sample. In one embodiment, compositions and methods are provided for analyzing a plurality of polymorphisms in a nucleic acid sample of fetal origin; and analyzing a plurality of polymorphisms in a nucleic acid sample of maternal origin, whereby the presence of at least one polymorphism in the nucleic acid sample of fetal origin, which is not present in the nucleic acid sample of maternal origin, confirms the presence of fetal nucleic acid in the fetal nucleic acid sample. In a related embodiment, the presence of at least one polymorphism in the nucleic acid sample of fetal origin, which is not present in the nucleic acid sample of maternal origin, is a paternally-inherited allele. In some embodiments, the same polymorphisms are analyzed in fetal nucleic acid and maternal nucleic acid. In some embodiments, the polymorphism is heterozygous. The plurality of polymorphisms may include 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000 or more polymorphisms. In a related embodiment, the polymorphism is a single nucleotide polymorphism (SNP), insertion/deletion, short tandem repeats (STRs), RFLPs or any other alternate form of a gene, genomic DNA or non-coding region of DNA that occupies the same position on a chromosome. The polymorphism may be naturally-occurring or synthetic. Synthetic polymorphisms may include alternative forms introduced on a synthetic oligonucleotide that serve as a competitor or control.

In a related embodiment, the invention in part provides compositions and methods of determining the presence or absence of fetal nucleic acid in the sample using the fetal identifiers set forth in Table 3 or 4. In one embodiment, the method of detecting the presence or absence of fetal nucleic acid in a sample comprises obtaining or possessing a nucleic acid sample known to be of maternal origin and suspected of comprising fetal nucleic acid; analyzing the nucleic acid sample to determine the maternal genotype of at one or more nucleotide polymorphisms selected from the group consisting of the polymorphisms set forth in Table 3 or 4; and analyzing the nucleic acid sample to determine the fetal genotype of one or more nucleotide polymorphisms selected from the group consisting of the polymorphisms set forth in Table 3 or 4, wherein a fetal genotype possessing a paternally-inherited allele indicates the presence of fetal nucleic acid. In a related embodiment, the maternal genotypes are determined from DNA that is substantially free of fetal nucleic acid. For example, in the case when the sample is blood, the maternal genotypes may be determined from the portion of the blood that comprises nucleated maternal cells (e.g., white blood cells). In one embodiment, the DNA that is substantially free of fetal nucleic acid is from peripheral blood mononuclear cells. In some embodiments, the amount of fetal DNA is determined by comparing the relative amount of paternally-inherited alleles to maternally-inherited alleles in fetal nucleic acid.

In certain embodiments, the compositions and methods of the invention may be used to detect the presence or absence of the Y-chromosome in a maternal sample, which may be used to determine the sex of a fetus. The presence or absence of the Y-chromosome in a maternal sample may be determined by performing the SRY assay provided herein. The SRY assay is a highly sensitive quantitative internal standard assay that detects trace amounts of the Y-chromosome.

The presence or absence of the Y-chromosome in a maternal sample may also be determined by performing the AMG assay provided herein. The presence or absence of a target nucleic acid may be determined in combination with other assays, such as an RhD assay or sex test assay. The methods may also be used for other applications, including but not limited to, paternity testing, forensics or quality control assays.

The invention in part also provides compositions and methods to determine the relative amount of target nucleic acid in a sample (e.g., fetal nucleic acid in a pregnant female sample). In one embodiment, the compositions and methods of the invention may be used to quantitate the relative amount of the alleles at a heterozygous polymorphic site, wherein said heterozygous polymorphic site has been identified by determining the sequence of alleles at a polymorphic site from template DNA obtained from a maternal sample, wherein said relative amount is expressed as a ratio, wherein said ratio indicates the relative amount of fetal nucleic acid present in the maternal sample. In a related embodiment, the polymorphic sites are provided in Table 3 or 4, 3 or 4. In some embodiments, the polymorphic site is an insertion/deletion, STR or RFLP.

In a related embodiment, the invention in part provides compositions and methods to determine the relative amount of fetal DNA in a sample (e.g., plasma of a pregnant woman carrying a male fetus), which comprises annealing one or more X and Y-specific AMG sequences to the fetal DNA, the primers provided in FIG. 3A-3C; performing a primer extension reaction; and analyzing the primer extension products to determine the ratio of the X and Y-specific extension products. In a related embodiment, the fetal AMG amplicon is first amplified using the amplification primers provided in FIGS. 3A-3C. In another related embodiment, the competitors provided in FIGS. 3A-3C are introduced as an internal standard to determine copy number.

In a related embodiment, the invention in part provides compositions and methods to determine the relative amount of target nucleic acid in a sample (e.g., fetal nucleic acid in plasma of a pregnant woman carrying a male fetus). In one embodiment, one or more Y-specific SRY sequences are annealed to the fetal DNA, the primer comprising GTTAC-CCGATTGTCCTAC (SEQ ID NO: 23); performing a primer extension reaction; and analyzing the primer extension products to determine the presence and relative amount of Y-specific extension products. In a related embodiment, the fetal SRY amplicon is first amplified using the following amplification primer pair:

```
                                        (SEQ ID NO: 24)
ACGTTGGATGAGCATCTAGGTAGGTCTTTG
and (SEQ ID NO: 25)
ACGTTGGATGAGCAACGGGACCGCTACAG.
```

In some embodiments, the total copy number of nucleic acid molecules for the human serum albumin (ALB) gene is determined. Methods for determining the total copy number of nucleic acid present in a sample comprise detecting albumin-specific extension products and comparing the relative amount of the extension products to competitors introduced to the sample. In a related embodiment, the invention in part provides compositions and methods to determine the relative amount of fetal DNA in a sample (e.g., plasma of a pregnant woman carrying a male fetus), which comprises annealing one or more albumin gene sequences to the fetal DNA, the primers provided in FIG. 4; performing a primer extension reaction; and analyzing the primer extension products to determine the relative amount of ALB extension products. In a related embodiment, the fetal ALB amplicon is first amplified using the amplification primers provided in FIG. 4. The assay is useful to measure how much nucleic acid (e.g., total copy number) is present in a sample or loaded into a particular reaction. The assay may serve as an internal control and a guide to the likelihood of success for a particular PCR reaction. For example, if only 400 copies of ALB are measured then the probability of detecting any fetal DNA may be considered low. In another related embodiment, the competitors provided in FIG. 4 are introduced as an internal standard to determine copy number. In one embodiment, 200, 300, 400, 500, 600, 700, 800 or more competitors are introduced to the assay.

The methods of the present invention may be performed alone or in combination with other tests.

In one embodiment the sample is blood. In certain embodiments, the sample is blood from a pregnant female. In a related embodiment, the blood is obtained from a human pregnant female when the fetus is at a gestational age selected from the group consisting of: 0-4, 4-8, 8-12, 12-16, 16-20, 20-24, 24-28, 28-32, 32-36, 36-40, 40-44, 44-48, 48-52, and more than 52 weeks. In another related embodiment, the sample is obtained through non-invasive means. In some embodiments, the nucleic acid is obtained from plasma from said blood. In some embodiments, the nucleic acid is obtained from serum from said blood. In some embodiments, the sample comprises a mixture of maternal DNA and fetal DNA. While the invention is not limited by how the sample is obtained, the methods and compositions of the invention are particularly useful for assaying samples obtained by non-invasive means, which may contain lower amounts of nucleic acid to be assayed. In a related embodiment, the sample is processed to selectively enrich fetal nucleic acid. In another related embodiment, the maternal and fetal Rh genotypes are determined in a multiplexed assay, or a combination of two or more multiplexed reactions. In a further related embodiment, the maternal Rh genotype is determined by analyzing maternal nucleic acid from maternal nucleated cells, for example, peripheral mononuclear blood cells (PMBC).

The invention in part utilizes multiplexed reactions to improve throughput and reduce cost. Thus, provided herein are optimized methods for performing a primer mass extension assay, including an optimized PCR amplification reaction that produces amplified targets for subsequent multiplexed primer mass extension genotyping analysis using mass spectrometry. Also provided herein are optimized methods for performing multiplexed amplification reactions and multiplexed primer mass extension reactions in a single well to further increase the throughput and reduce the cost per genotype for primer mass extension reactions. The nucleic acid target-region amplification and primer mass extension genotyping reactions have been optimized herein to permit moderate to high level multiplexing reactions with greater efficiency and accuracy, while at the same time not adversely affecting the mass spectrometry analysis of mass extension products.

In one embodiment, the amplification primers provided in Table 3 comprises a 5' tag and a gene-specific sequence (underlined). The tag is used to assist in the amplification of the nucleic acids. The primer tags may serve to stabilize the primer during amplification or they may serve as universal primer sites. More specifically, once the RhD gene nucleic acids have been PCR amplified using the primers, primers to the tags are used to further amplify the sequences. In one embodiment, both amplification steps are performed simultaneously. As will be appreciated by those skilled in the art, primers without the 5' tag (primer sequences underlined in the Table) can be used in the method of the invention in order to amplify the RhD gene nucleic acids. Alternatively, the primer sequences can comprise different tag sequences than the tags indicated in the Table. Tag sequences useful for multiplex amplification reactions are well known in the art.

In some embodiments, the amplification primers allow for sequence specific amplification. For example, the PCR primers are designed to discriminate against amplification of the RHCE gene by taking advantage of sequence differences between the RHD and RHCE gene. In some embodiments, the extend primer of the post-PCR primer extension reaction is designed to target a sequence difference between RHD and RHCE gene so that any leakage in the allele-specific amplification would lead to a distinguishable primer extension product that does not interfere with correct interpretation of RHD detection.

In particular embodiments, a sequence tag is attached to a plurality of primary and secondary primer pairs provided in Table 3. The sequence tag can be attached to either one or both of the primary and secondary primers from each pair. Typically, the sequence tag is attached to the primary and secondary primer of each pair. The sequence tags used herein can range from 5 up to 20, from 5 up to 30, from 5 up to 40, or from 5 up to 50 nucleotides in length, with a sequence tag of 10-mer length being particularly useful in the methods provided herein. The sequence tag need not be the same sequence for each primer pair in the multiplexed amplification reaction, nor the same sequence for a primary and secondary primer within a particular amplification pair. In a particular embodiment, the sequence tag is the same for each primer in the multiplexed amplification reaction. For example, in certain embodiments, the sequence tag is a 10-mer, such as -ACGT-TGGATG- (SEQ ID NO: 26), and is attached to the 5' end of each primary and secondary primer. In particular embodiments of the methods provided herein, only a single primer pair is used to amplify each particular nucleic acid target-region.

BRIEF DESCRIPTION OF THE DRAWINGS

FIG. 1A-1F provide the location design of the RhD primers. The amplification primers are highlighted and the extend primers are in bold. The Figures also provide the extend primer product associated with each respective assay result. For example, in FIG. 1A, an extension product with an adenine (A) chain terminating nucleotide indicates the presence of exon 4 of the RhD gene, an extension product with an adenine and a thymine (A & T) chain terminating nucleotide indicates the presence of exon 4 of the RhD psi pseudogene, and an extension product with a cytosine (C) chain terminating nucleotide indicates the presence of exon 4 of the RHCE gene. FIG. 1A discloses SEQ ID NOS 5-6, 18 and 174-176, respectively, in order of appearance. FIG. 1B discloses SEQ ID NOS 3-4, 177 and 174-175, respectively, in order of appearance. FIG. 1C discloses SEQ ID NOS 7-8, 19-20 and 178-179, respectively, in order of appearance. FIG. 1D discloses SEQ ID NOS 180-184, respectively, in order of appearance. FIG. 1E discloses SEQ ID NOS 11, 10 and 185-187, respectively, in order of appearance. FIG. 1F discloses SEQ ID NOS 12-13 and 188-190, respectively, in order of appearance.

FIG. 2 provides the location design of the SRY primers in the SRY gene coding sequence (SEQ ID NO: 191). The amplification primers are highlighted and the extend primers are underlined. Where the PCR primers are provided alone, the sequence-specific portion of the primer is underlined, and the multiplex tag is not underlined. In addition, competitor sequences are provided. FIG. 2 discloses SEQ ID NOS 192-201, 25, 24, 202-212, respectively, in order of appearance.

FIG. 3A-3C provide the location design of the AMG primers. The amplification primers are underlined once and the extend primers are underlined twice. In addition, competitor sequences are provided. FIG. 3C includes a Results Table that shows the different masses generated by each of the AMG and SRY assays, which may be used to interpret the results from the assays. FIG. 3A discloses SEQ ID NOS 213-221, respectively, in order of appearance. FIG. 3B discloses SEQ ID NOS 213-214 and 222-226, respectively, in order of appearance. FIG. 3C discloses SEQ ID NOS 213-241, 227-228, 217, 229-231, 217, 230, 232-233, 194 and 234, respectively, in order of appearance.

FIG. 4 provides the location design of the albumin (ALB) primers. The amplification primers are highlighted and the extend primer is underlined twice. Where the PCR primers are provided alone, the sequence-specific portion of the primer is underlined, and the multiplex tag is not underlined. In addition, competitor sequences are provided. FIG. 4 discloses SEQ ID NOS 235-241, respectively, in order of appearance.

DETAILED DESCRIPTION

Figure 5:
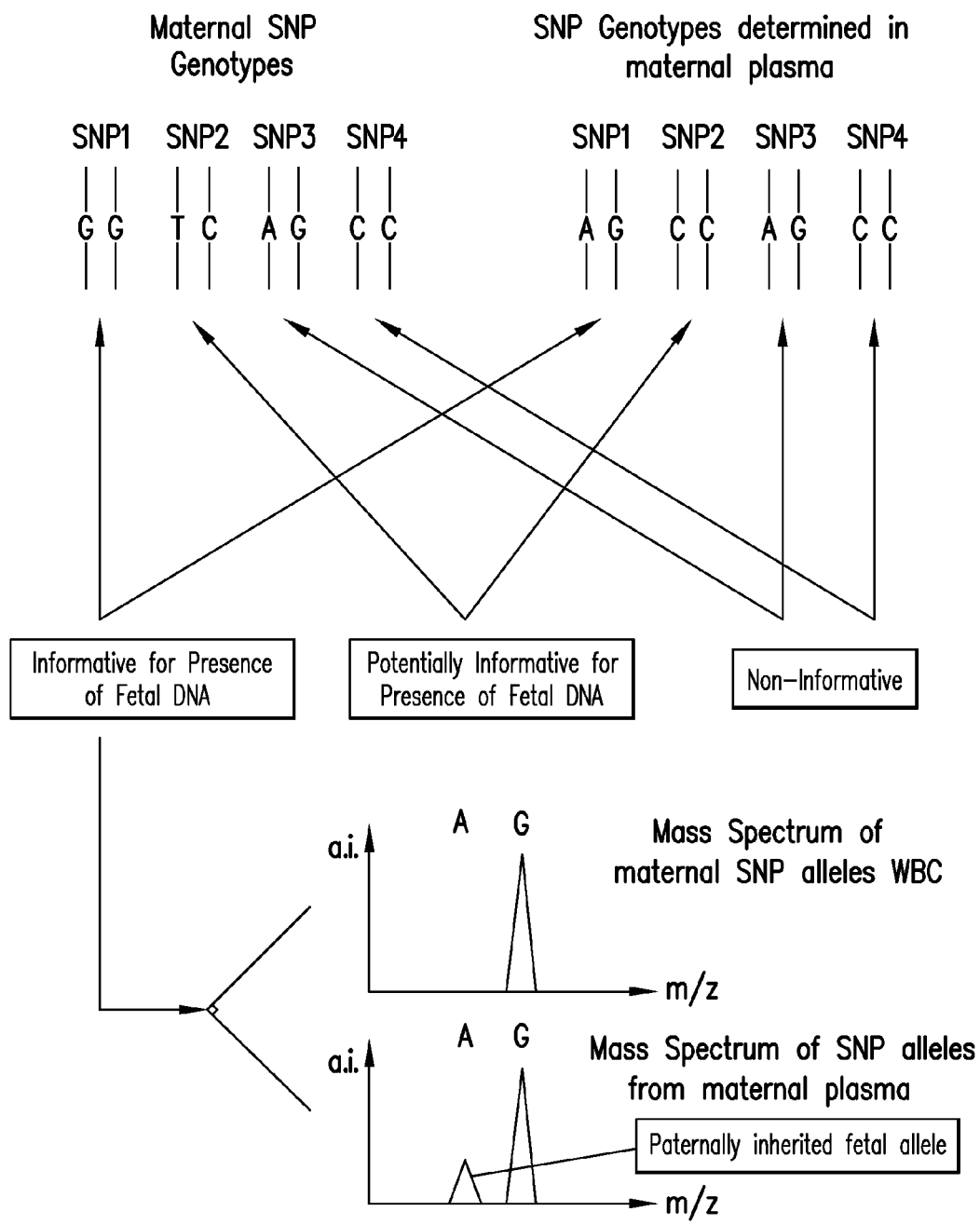
FIG. 5 shows the use of single nucleotide polymorphisms (SNP's) Fetal Identifiers to confirm the presence of fetal DNA by paternally-inherited alleles.

The determination of fetal Rh genotypes from maternal plasma is usually performed by PCR amplification of individual RhD exons. Negative test results, in particular for female fetuses, can require additional tests confirming the presence of sufficient amounts of fetal DNA. The compositions and methods of the invention offer nucleic acid-based tests for determining Rh type and determining the relative amount of target nucleic acid in a sample. The tests are particularly useful for prenatal diagnostics, wherein the presence and relative amount of fetal nucleic acid in a maternal sample can be determined, and further wherein fetal and maternal Rh type can be determined in a highly sensitive, accurate multiplexed reaction. The invention, therefore, provides an alternative method that further comprises high-frequency single nucleotide polymorphisms (SNPs) to determine the amount of fetal nucleic acid present in a sample, which in turn reduces the number of inconclusive tests.

The test primers were designed to ensure that the exon sequence for exons 4, 5, 7 and 10 inclusive of RhD is amplified by the RhD MPX PCR of the invention. The location design of the RhD primers is illustrated in FIGS. 1A-1F.

The assays provided herein offer many advantageous over existing RhD typing methods. Specifically, the multiplexed test reagents address the limited availability of fetal nucleic acid, complexity of genetic changes and high quality testing. The multiplexed RhD/Fetal Identifier assays allow for comprehensive non-invasive Rh genotyping of fetal DNA in only two reactions, while guarding against false-interpretation of negative test results caused by insufficient amounts of fetal DNA. Alternatively, the reactions are performed in a single, multiplexed reaction. The assays have built in quality controls to improve the accuracy of results. The RhDψ pseudogene is recognized even in heterozygote state. The SRY assay is highly sensitive and specific for paternal alleles, and the determination of maternal baseline requires only one additional reaction. Finally, the assay can be used for analysis of adult blood donor subjects. This is important in connection with subjects who receive frequent transfusions, for example, those with sickle cell anemia.

In one embodiment, the invention also relates to a method for determining whether a patient in need of a blood transfusion is to be transfused with RhD negative blood from a donor. The invention has important implications for devising a transfusion therapy in humans. For example, it can now be conveniently tested whether the patient actually needs a transfusion with a RhD negative blood or whether such precautions need not be taken.

As used herein, "sample" refers to a composition containing a material to be detected or analyzed. Samples include "biological samples", which refer to any material obtained from a living source, for example, an animal such as a human or other mammal, a plant, a bacterium, a fungus, a protist or a virus or a processed form, such as amplified or isolated material. The sample may be obtained through invasive (e.g., amniocentesis) or non-invasive (e.g., blood draw) means. In a preferred embodiment, the sample is obtained non-invasively. The biological sample can be in any form, including a solid material such as a tissue, cells, a cell pellet, a cell extract, a biopsy, or feces, or a biological fluid such as urine, whole blood, plasma, serum, interstitial fluid, vaginal swab, pap smear, peritoneal fluid, lymph fluid, ascites, sweat, saliva, follicular fluid, breast milk, non-milk breast secretions, cerebral spinal fluid, seminal fluid, lung sputum, amniotic fluid, exudate from a region of infection or inflammation, a mouth wash containing buccal cells, synovial fluid, or any other fluid sample produced by the subject. In addition, the sample can be solid samples of tissues or organs, such as collected tissues, including bone marrow, epithelium, stomach, prostate, kidney, bladder, breast, colon, lung, pancreas, endometrium, neuron, muscle, and other tissues. Samples can include organs, and pathological samples such as a formalin-fixed sample embedded in paraffin. If desired, solid materials can be mixed with a fluid or purified or amplified or otherwise treated. Samples examined using the methods described herein can be treated in one or more purification steps in order to increase the purity of the desired cells or nucleic acid in the sample. Samples also can be examined using the methods described herein without any purification steps to increase the purity or relative concentration of desired cells or nucleic acid. As used herein, the term "blood" encompasses whole blood or any fractions of blood, such as serum and plasma as conventionally defined.

The terms "nucleic acid" and "nucleic acid molecule" may be used interchangeably throughout the disclosure. The terms refer to a deoxyribonucleotide (DNA), ribonucleotide polymer (RNA), RNA/DNA hybrids and polyamide nucleic acids (PNAs) in either single- or double-stranded form, and unless otherwise limited, would encompass known analogs of natural nucleotides that can function in a similar manner as naturally occurring nucleotides.

As used herein, the term "amplifying" or "amplification" refers to means for increasing the amount of a biopolymer, especially nucleic acids. Based on the 5' and 3' primers that are chosen, amplification also serves to restrict and define a target-region or locus of the genome which is subject to analysis. Amplification can be by any means known to those skilled in the art, and in particular embodiments, includes the use of the polymerase chain reaction (PCR). The phrase simultaneous amplification refers to the amplification of 2 or more nucleic acid target-regions at the same time. The simultaneous amplification is typically within the same amplification mixture.

As used herein, the term "multiplexing" refers to the simultaneous amplification or primer mass extension reaction of more than one oligonucleotide or primer (e.g., in a single reaction container); or the simultaneous analysis of more than one oligonucleotide, in a single mass spectrometric or other mass measurement, i.e., a single mass spectrum or other method of reading sequence.

As used herein, the phrase "simultaneous amplification" refers to the multiplexed amplification of 2 or more loci or nucleic acid target-regions in a single reaction mixture. Simultaneous amplification therefore encompasses 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 30 or more, 40 or more, 50 or more, 60 or more, 70 or more, 80 or more, 100 or more, 200 or more, 500 or more, 1000 or more, 2000 or more amplification reactions. The amplification of each particular target-region occurs in parallel at the same time. Although it is contemplated herein that the simultaneous amplifications can occur in separate reaction mixtures, for the methods provided herein the simultaneous amplification reactions typically occur in the same single reaction. Likewise multiplexed primer mass extension refers to the simultaneous extension of 2 or more genotyping primers in a single reaction mixture. Accordingly, multiplexed primer mass extension therefore encompasses [5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 30 or more, 40 or more, 50 or more, 60 or more, 70 or more, 80 or more, 100 or more, 200 or more, 500 or more, 1000 or more, 2000 or more primer mass extension reactions. Multiplexed amplification and primer mass extension reactions also encompass 21, 22, 23, 24, 24, 25, 26, 27, 28, 29, 30, 35, 40, 45, 50, 60, 70, 80, 100, 1000 or more reactions.

As used herein, the phrase "target nucleic acid" refers to one or more nucleic acids, such as genomic DNA, from which one or more regions or loci are to be amplified.

As used herein, the phrase "nucleic acid-target region" refers to the region-specific areas or loci of a target nucleic acid (e.g., UTR, exon or intron) that are amplified for subsequent sequence variation analysis. The amplified nucleic acid-target regions each contain at least one sequence variation or site that is being genotyped.

As used herein, the term "polymorphism" refers to the coexistence of more than one form or allele of a nucleic acid, such as a chromosome, or portion thereof. For example, a portion or locus of a gene at which there are at least two different alleles, i.e., two different nucleotide sequences, is referred to as a polymorphic loci, site or region of a gene. A polymorphic loci can be a single nucleotide (e.g., SNP) or can be several nucleotides in length (e.g., insertions or deletions). Accordingly, polymorphism includes substitutions, insertions, duplications and deletions of nucleotides. A polymorphism can also refer to a particular nucleotide(s) or nucleotide sequence occurring at a particular polymorphic site.

As used herein, the term "genotyping" refers to the process of determining the particular nucleotide or nucleotides (e.g., sequence variation) either present or absent at a particular polymorphic loci or genomic location.

As used herein, "allele", which is used interchangeably herein with "allelic variant" refers to alternative forms of a nucleic acid such as a gene or polymorphic regions thereof. Alleles occupy the same locus or position (referred to herein as a polymorphic region) on homologous chromosomes. When a subject has two identical alleles of a polymorphic region within a gene, the subject is said to be homozygous for the allele. When a subject has two different alleles of a polymorphic region within a gene, the subject is said to be heterozygous for the allele. Alleles of a specific gene can differ from each other at a polymorphic region corresponding to a single nucleotide, or several nucleotides, and can include substitutions, deletions, insertions and duplications of nucleotides. An allele of a gene can also be a form of a gene containing a mutation.

As used herein, the term "non-homologous variant" refers to one or more sequence variations that exist between two or more highly homologous genes (e.g., RhD and RHCE), pseudogenes, transcript variants, repeats or other similar genomic sequences. Non-homologous variants between genes can differ from each other by a single nucleotide, or several nucleotides, and can include substitutions, deletions, insertions and duplications of nucleotides. For example, an RhD pseudogene exists that contains a 37 base pair insertion in exon 4. In the context of the present invention, the 37 base pair insertion of the pseudogene is considered a non-homologous variant. Non-homologous variants usually occupy the same locus or position on highly homologous genes (e.g., in the same, corresponding exon or intron). For example, sequence variations between the highly homologous RhD and RHCE genes are particularly useful for RhD testing.

As used herein, the term "genotype" refers to the identity of the alleles or non-homologous variants present in an individual or sample. The term "genotyping a sample" or "genotyping an individual" refers to determining a specific allele or specific nucleotide(s) in a sample or carried by an individual at particular region(s).

As used herein, the phrase "RhD testing" refers to a DNA-based genotyping method to detect the RhD and/or RHCE genes and their prevalent alleles, non-homologous variants and combinations thereof (e.g., RhD sequence that contains replacements with homologous RHCE sequences). RhD testing may be used to determine an RhD phenotype.

As used herein, the term "Rh phenotype" refers to determining the presence or absence of antigens of the Rh blood group, specifically red cell antigens C, D and E. An individual is either Rh-positive or Rh-negative for a given antigen. For example, "an RhD-negative" individual does not express antigen D, whereas an RhD-positive individual does express antigen D. "Rh incompatibility" occurs when red cells from a Rhesus positive fetus cross the placenta and sensitize a Rhesus negative mother, especially at parturition. The mother's antibody may then, in a subsequent pregnancy, cause haemolytic disease of the newborn if the fetus is Rhesus positive.

Whether detecting sequence differences, detecting amplification products or primer extension products, any detection method known in the art may be utilized. While many detection methods include a process in which a DNA region carrying the polymorphic site of interest is amplified, ultra sensitive detection methods which do not require amplification may be utilized in the detection method, thereby eliminating the amplification process. Polymorphism detection methods known in the art include, for example, primer extension or microsequencing methods, ligase sequence determination methods (e.g., U.S. Pat. Nos. 5,679,524 and 5,952,174, and WO 01/27326), mismatch sequence determination methods (e.g., U.S. Pat. Nos. 5,851,770; 5,958,692; 6,110,684; and 6,183,958), microarray sequence determination methods, restriction fragment length polymorphism (RFLP) procedures, PCR-based assays (e.g., TAQMAN® PCR System (Applied Biosystems)), nucleotide sequencing methods, hybridization methods, conventional dot blot analyses, single strand conformational polymorphism analysis (SSCP, e.g., U.S. Pat. Nos. 5,891,625 and 6,013,499; Orita et al., *Proc. Natl. Acad. Sci. U.S.A* 86: 27776-2770 (1989)), denaturing gradient gel electrophoresis (DGGE), heteroduplex analysis, mismatch cleavage detection, and techniques described in Sheffield et al., *Proc. Natl. Acad. Sci. USA* 49: 699-706 (1991), White et al., *Genomics* 12: 301-306 (1992), Grompe et al., *Proc. Natl. Acad. Sci. USA* 86: 5855-5892 (1989), and Grompe, *Nature Genetics* 5: 111-117 (1993), detection by mass spectrometry (e.g., US 20050079521, which is hereby incorporated by reference), real time-PCR (e.g., U.S. Pat. No. 5,210,015, U.S. Pat. No. 5,487,972, both of which are hereby incorporated by reference), or hybridization with a suitable nucleic acid primer specific for the sequence to be detected. Suitable nucleic acid primers can be provided in a format such as a gene chip.

Primer extension polymorphism detection methods, also referred to herein as "microsequencing" methods, typically are carried out by hybridizing a complementary oligonucleotide to a nucleic acid carrying the polymorphic site. In these methods, the oligonucleotide typically hybridizes adjacent to the polymorphic site. As used herein, the term "adjacent" refers to the 3' end of the extension oligonucleotide being sometimes 1 nucleotide from the 5' end of the polymorphic site, often 2 or 3, and at times 4, 5, 6, 7, 8, 9, or 10 nucleotides from the 5' end of the polymorphic site, in the nucleic acid when the extension oligonucleotide is hybridized to the nucleic acid. The extension oligonucleotide then is extended by one or more nucleotides, often 1, 2, or 3 nucleotides, and the number and/or type of nucleotides that are added to the extension oligonucleotide determine which polymorphic variant or variants are present. Oligonucleotide extension methods are disclosed, for example, in U.S. Pat. Nos. 4,656,127; 4,851,331; 5,679,524; 5,834,189; 5,876,934; 5,908,755; 5,912,118; 5,976,802; 5,981,186; 6,004,744; 6,013,431; 6,017,702; 6,046,005; 6,087,095; 6,210,891; and WO 01/20039. The extension products can be detected in any manner, such as by fluorescence methods (see, e.g., Chen & Kwok, *Nucleic Acids Research* 25: 347-353 (1997) and Chen et al., *Proc. Natl. Acad. Sci. USA* 94/20: 10756-10761 (1997)) and by mass spectrometric methods (e.g., MALDI-TOF mass spectrometry or electrospray mass spectrometry). Oligonucleotide extension methods using mass spectrometry are described, for example, in U.S. Pat. Nos. 5,547,835; 5,605,798; 5,691,141; 5,849,542; 5,869,242; 5,928,906; 6,043,031; 6,194,144; and 6,258,538.

Microsequencing detection methods often incorporate an amplification process that proceeds the extension step. The amplification process typically amplifies a region from a nucleic acid sample that comprises the polymorphic site. Amplification can be carried out by utilizing a pair of oligonucleotide primers in a polymerase chain reaction (PCR), in which one oligonucleotide primer typically is complementary to a region 3' of the polymorphism and the other typically is complementary to a region 5' of the polymorphism. A PCR primer pair may be used in methods disclosed in U.S. Pat. Nos. 4,683,195; 4,683,202, 4,965,188; 5,656,493; 5,998,143; 6,140,054; WO 01/27327; and WO 01/27329 for example. PCR primer pairs may also be used in any commercially available machines that perform PCR, such as any of the GENEAMP® Systems available from Applied Biosystems.

A microarray can be utilized for determining whether a polymorphic variant is present or absent in a nucleic acid sample. A microarray may include any oligonucleotides described herein, and methods for making and using oligonucleotide microarrays suitable for prognostic use are disclosed in U.S. Pat. Nos. 5,492,806; 5,525,464; 5,589,330; 5,695,940; 5,849,483; 6,018,041; 6,045,996; 6,136,541; 6,142,681; 6,156,501; 6,197,506; 6,223,127; 6,225,625; 6,229,911; 6,239,273; WO 00/52625; WO 01/25485; and WO 01/29259. The microarray typically comprises a solid support and the oligonucleotides may be linked to this solid support by covalent bonds or by non-covalent interactions. The oligonucleotides may also be linked to the solid support directly or by a spacer molecule. A microarray may comprise one or more oligonucleotides complementary to a polymorphic site within a nucleotide sequence in Tables 6, 7 or 8.

Fetal Identifiers

Cell-free fetal DNA constitutes only a minor fraction of the total DNA found in maternal plasma. The amount of fetal DNA in maternal plasma is dependent on the gestational age and is estimated at 3-6%.

Because the analysis is relying on the detection of a paternally-inherited disease-causing sequence, it is vital to be able to ascertain that the absence of the disease-causing sequence is a true diagnostic result and not caused by insufficient amount of circulating fetal DNA or even loss of the fetal DNA during sample processing.

The use of polymorphisms provide a means to confirm the presence of fetal DNA and therefore complete the analysis of negative, and otherwise inconclusive, test result in non-invasive prenatal diagnostics. The use of single nucleotide polymorphisms (SNPs), the most abundant type of polymorphism in the human genome, or insertion/deletion (Ins/Del) polymorphisms may serve as fetal identifiers to determine the presence of fetal DNA in a processed sample (Li, Y., Wenzel, F., Holzgreve, W., Hahn, S., Genotyping fetal paternally inherited SNPs by MALDI-TOF MS using cell-free fetal DNA in maternal plasma: Influence of size fractionation. Electrophoresis 27, 3889-3896 (2006); Van der Schoot, C. E., Rijnders, R. J., Bossers, B., de Haas, M., Christiaens, G. C., Dee, R. Real-time PCR of bi-allelic insertion/deletion polymorphisms can serve as a reliable positive control for cell-free fetal DNA in non-invasive prenatal genotyping [abstract] Blood 102, 93a (2003); and Chow, K. C., Chiu, R. W., Tsui, N. B., Ding, C., Lau, T. K., Leung, T. N., Lo, Y. M., Mass Spectrometric detection of a SNP panel as an internal positive control for fetal DNA analysis in maternal plasma. Clin. Chem. 53, 141-142 (2007), all of which are hereby incorporated by reference).

A SNP is considered informative for the determination of the presence of fetal DNA, if the mother is homozygous and the fetus inherited the opposite allele from the father, rendering the genotype of the fetus heterozygous.

To ensure a high probability that the presence of fetal DNA can be confirmed by the presence of the paternally-inherited allele in at least 1 SNP, a sufficient number of SNPs or Ins/Dels with a high population frequency (>0.4 for the minor frequent allele) has to be analyzed. A scheme exemplifying the concept of using SNPs to confirm the presence of fetal DNA in maternal plasma is depicted in FIG. 5.

Analysis of multiple polymorphisms in DNA extracted from maternal plasma creates a two-fold challenge: firstly, the paternally-inherited allele needs to be detected in the background of the maternal DNA; secondly, the high number of polymorphisms require significant sample material and a significant number of reactions before a conclusive test result is achieved.

Thus the invention in part provides a multiplexed panel of SNPs to establish a universal assay panel for non-invasive prenatal diagnostics.

Kits

Furthermore, the invention relates to a kit comprising the compositions of the invention. Parts of the kit can be packaged individually in vials or in combination in containers or multicontainer units. The kit of the present invention may be advantageously used for carrying out the method of the invention and could be, inter alia, employed in a variety of applications referred to above. The manufacture of the kits follows preferably standard procedures which are known to people skilled in the art.

EXAMPLES

The following examples illustrate but do not limit the invention.

Example 1

RhD Test

Analysis of RhD exons and SNPs was enabled by multiplex PCR followed by multiplexed allele-specific primer extension and analysis by MALDI-TOF MS. Initial evaluation of the assays was performed using genomic DNA. Multiplexes were also evaluated from artificial mixtures to establish sensitivity and precision of the semi-quantitative readout of SNP alleles. Final performance was established using cell-free fetal DNA from maternal plasma.

Extraction of cell-free fetal DNA was performed using a modified Qiagen MinElute protocol.

Two multiplex reactions were developed that cumulatively integrated the detection of RhD exons 4, 5, 7, 10 and the detection of the RhD psi pseudogene conversion with 16 high-frequent SNPs. The use of 16 SNPs statistically provides up to 4 assays, which can confirm the presence of fetal DNA through detection of the paternally-inherited fetal allele. Performance of the multiplexed assays in artificial mixtures and in cell-free fetal DNA extracted from maternal plasma was demonstrated.

The method comprises the following 8 steps:
1. Isolate plasma and peripheral blood mononuclear cells (PBMC) from whole blood.
2. Purify cell-free DNA from the plasma (designated fetal DNA).
3. Purify DNA from PBMC (designated maternal DNA).
4. Prepare fetal and maternal DNA working dilutions (0.15 ng/µl).
5. Amplify the fetal and maternal DNA.
6. Process the Iplex™ Gold extend reactions on the amplified fetal and maternal DNA.
7. Dispense the MassExtend reaction products to a SpectroCH IP® array.
8. Analyze samples on the MassARRAY Analyzer Compact.
9. Interpret the results using with the aid of Table 1.

TABLE 1

RhD Test Interpretation

| | RhD/ RhD psi Exon 4 | RhD/ RhD psi Exon 4 | RhD Exon 5 | RhD Exon 7 | RhD Exon 10 | Test Interpretation |
|---|---|---|---|---|---|---|
| Gene deletion | <u>C</u> | <u>G</u> | <u>C</u> | <u>C</u> | — | RhD– |
| Gene conversion RhD-CE-D; exons 1 and 10 of RhD gene present | <u>C</u> | <u>G</u> | <u>C</u> | <u>C</u> | T | RhD– |
| Gene conversion RhD-CE-D; exons 1-3 and 9-10 of RhD gene present | C | G | C | C | T | RhD– |
| Pseudogene RhDψ homozygous | AT | A | G | T | T | RhD– |
| Pseudogene RhDψ heterzygous | AT | AG | G | T | T | RhD+ |
| Apparently intact RhD gene; possibly bearing | A | G | G | T | T | RhD+ |

TABLE 1-continued

RhD Test Interpretation

| | RhD/<br>RhD psi<br>Exon 4 | RhD/<br>RhD psi<br>Exon 4 | RhD<br>Exon 5 | RhD<br>Exon 7 | RhD<br>Exon 10 | Test Interpretation |
|---|---|---|---|---|---|---|
| single point mutations | | | | | | |

RhCE alleles denoted in bold and underlined represent leakage from allele-specific priming.

Any negative result is a true negative.

Any positive result is a true positive.

Inconclusive results will result in further testing and/or therapy.

Step 5 and 6 are further described herein. Following genomic amplification, the assay interrogates amplified regions through the use of specific primers that are designed to hybridize directly adjacent to the site of interest. These DNA oligonucleotides are referred to as iPLEX MassEXTEND primers. In the extension reaction, the iPLEX primers are hybridized to the complementary DNA templates and extended with a DNA polymerase. Special termination mixtures that contain different combinations of deoxy- and dideoxynucleotide triphosphates along with enzyme and buffer, direct limited extension of the iPLEX primers. Primer extension occurs until a complementary dideoxynucleotide is incorporated.

The extension reaction generates primer products of varying length, each with a unique molecular weight. As a result, the primer extension products can be simultaneously separated and detected using Matrix Assisted Laser Desorption/Ionization, Time-Of-Flight(MALDI-TOF) mass spectrometry on the MassARRAY® Analyzer Compact. Following this separation and detection, SEQUENOM's proprietary software automatically analyzes the data and presents the assay results in the BioReporter RhD report.

A more specific protocol is provided in the Tables below. These conditions are not intended to limit the scope of the invention.

TABLE A

PCR Master Mix Preparation (MMX)

| MMX | Reagent | Final Conc. per 50 μl rxn | Volume per each 50 μl (ul) | Volume per 100 rxn (ul) |
|---|---|---|---|---|
| MMX1 | Water | N/A | 7.55 | 755 |
| | 10×PCR Buffer (contains 15 mM MgCl2, Tris-Cl, KCl, (NH4)2SO4, pH 8.7 (Qiagen) | 1.25x | 6.25 | 625 |
| | 25 mM MgCl₂ (Qiagen) | 1.625 mM | 3.25 | 325 |
| | PCR Nucleotide Mix (10 mM each dATP, dCTP, dGTP, dUTP) (Roche) | 800 μM (200 uM each) | 1 | 100 |
| | 2 U/μl Uracil-DNA-Glycosylase (UDG)(NEB) | 2.5 U/rxn | 1.25 | 125 |
| | 5 U/μl HotStar Taq (Qiagen) | 3.5 U/rxn | 0.7 | 70 |
| | Sub Total for MMX1 | | 20 | 2000 |
| MMX2 | 0.5-1.5 uM RhD primers Mix (Operon/IDT) | 0.1-0.5 uM each | 10 | 1000 |
| MMX Sample | Total for MMX | | 30 | 3000 |
| | DNA ng/ul | | 20 | |
| | PCR Reaction Total | | 50 | |

1.2.1 Combine 20 ul of MMX1 and 10 ul of MMX2 to make 30 ul of each PCR MMX.

1.2.2 Add 20 ul of sample (plasma DNA) to MMX 1.2.3 Mix well, seal plate, spin briefly and cycle according to following parameters in table 3.

TABLE B

PCR 30-11Cycling Conditions (two steps cycling)

| Temp. | Time | Cycles | Notes |
|---|---|---|---|
| 30 C. | 10 min | 1 | UDG Incubation |
| 94 C. | 15 min | 1 | Initial Denaturation |
| 94 C. | 20 sec | | Target Amplification |
| 56 C. | 30 sec | 30 cycles | |
| 72 C. | 1 min | | |
| 94 C. | 20 sec | | Product Amplification |
| 62 C. | 30 sec | 11 cycles | |
| 72 C. | 1 min | | |
| 72 C. | 3 min | 1 | Final Extension |
| 4 C. | Forever | 1 | Hold |

1.2.4 10 uL PCR Aliquots

Prepare two iPLEX EXTEND reaction plates by plating 10 uL PCR samples from each well of the PCR plate into two new 96-well plates designated for SAP and EXTEND reactions using the liquid handler 1.3 SAP Reaction 1.3.1 Prepare the SAP mixes according to Table 4 below. Dispense 6 μA SAP mix to the corresponding wells of one V-bottom Sarstedt 96-well plate. Transfer 4 μl SAP from the 96-well stock plate to each of the 96-well PCR plates, using a Liquid Handler.

TABLE C

SAP Cocktail preparation

| Reagent | Final C | n = 1 | Volume [uL] (60% overhang) 160 | Lot# |
|---|---|---|---|---|
| Nanopure Water, Autoclaved | n/a | 2.95 | 472 | |
| SAP Buffer, 10× | 0.85x | 0.34 | 54.4 | |

TABLE C-continued

SAP Cocktail preparation

| Reagent | Final C | n = 1 | Volume [uL] (60% overhang) 160 | Lot# |
|---|---|---|---|---|
| SAP (1.7 U/ul = transparent label) | 1.2 U/rxn | 0.71 | 113.6 | |
| Total volume [uL] | n/a | 4 | 640 | n/a |

1.3.2 When preparation is finished, seal the plate, vortex, centrifuge briefly and cycle each plate according to the following parameters in the table below.

TABLE D

SAP Thermal Cycling Conditions

| Temperature | Incubation Time | Plate ID |
|---|---|---|
| 37° C. | 40 minutes | Program ID: SAP-40-5 |
| 80° C. | 5 minutes | |
| 4° C. | store | |

1.4 iPLEX Extension

TABLE E iPLEX EXTEND Cocktail Mix Preparation

| Extend Reagent | Volume = 1 - Rxn | Volume [uL] (60% overhang) 160 |
|---|---|---|
| Water (HPLC grade) | 1.238 | 198.08 |
| iPLEX detergent free buffer (10×) | 0.4 | 64 |
| iPLEX Termination Mix | 0.4 | 64 |
| Extend Primer Mix | 1.88 | 300.8 |
| Thermosequenase (32 U/uL) | 0.082 | 13.12 |
| Total Volume | 4 | 640 |

1.4.1 Add 6 ul cocktail to each well of one V-bottom Sarstedt 96 plate. Transfer 4 μl iPLEX-EXTEND cocktail from the V-bottom Sarstedt 96 plate to each well of the 96-SAP/PCR plates, using a Matrix MassARRAY Liquid Handler into well positions according to plate lay out.

1.4.2 Seal the plates, vortex, centrifuge briefly and cycle according to the parameters listed below in Table 10.

TABLE F hME-100

| Temperature | Incubation Time | Cycles | Notes |
|---|---|---|---|
| 94° C. | 2 minutes | 1 | Plate ID: |
| | | | 1) 06-28-2006_HLBK_ST_DOL |
| 94° C. | 5 seconds | 99 cycles | Program ID: hME-100 |
| 52° C. | 5 seconds | | Cycler ID: |
| | | | BLK0116, BSE 0046 |
| 72° C. | 5 seconds | | Cycler Bonnet ID (iM applicable): |
| 4° C. | forever | 1 | |

Example 2

Fetal Identifiers, Sex Test and Copy Number Determination

Selection of SNPs

Analysis of paternally-inherited alleles in clinical samples and correlation with Y-chromosome frequency in male fetuses was performed with a total of 16 SNPs; SNP assays for analysis of clinical samples were multiplexed as 8-plexes; all SNPs had a minor allele frequency (maf) of ~0.4 in all ethnic groups and were unlinked.

For performance evaluation of a universal Fetal Identifier panel that can be multiplexed with disease-specific markers, a new panel of 87 NT SNPs with a pan-ethnic maf >0.4 was selected and multiplexed into 16-plexes.

Method of SNP Analysis

Figure 6:
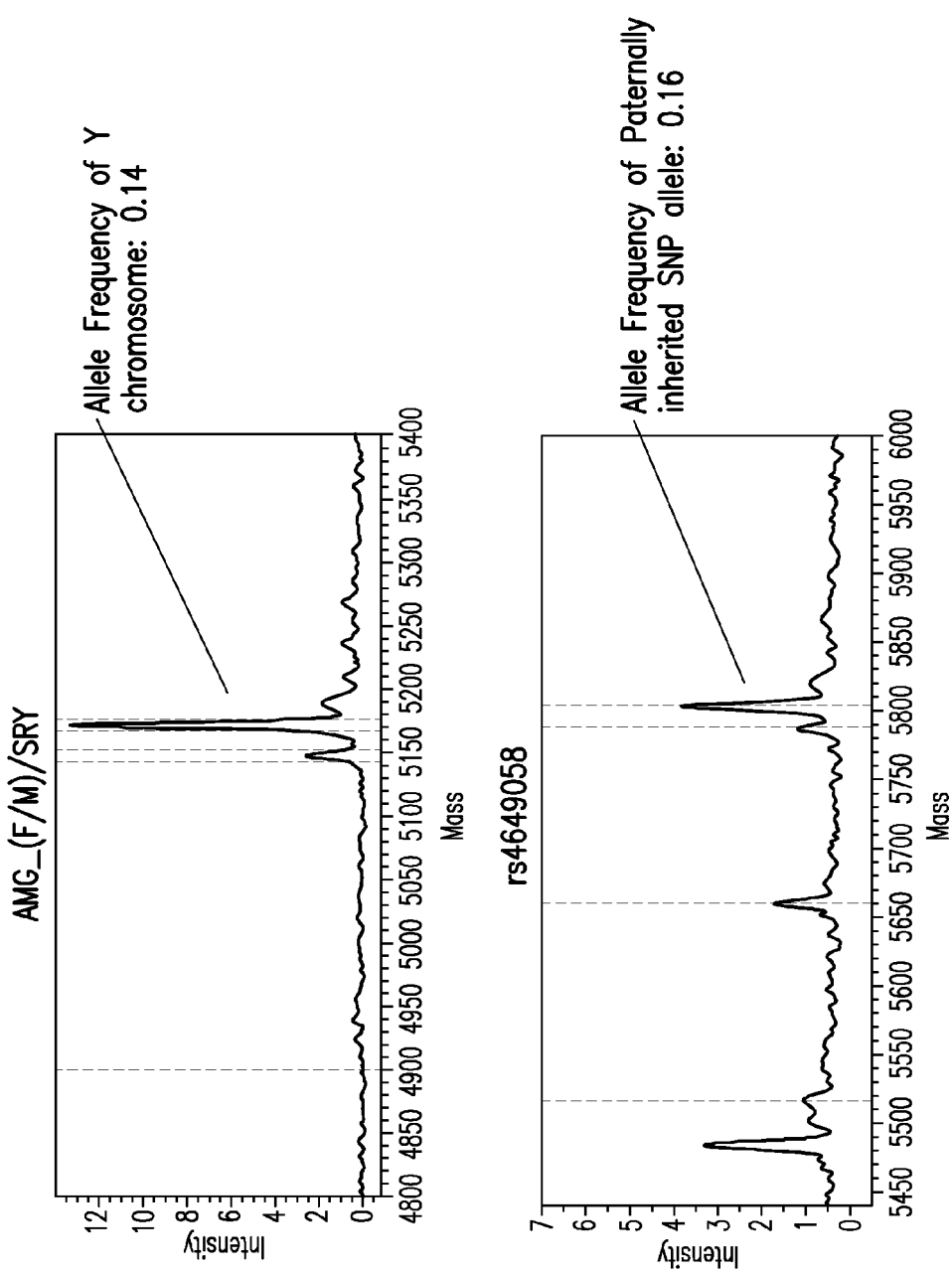
FIG. 6 shows representative mass spectra demonstrating the correlation between fetal DNA amounts estimated from AMG XY and from Fetal Identifier assays. The results were generated using the AMG primers provided in FIG. 3.

Analysis of SNPs in maternal buffy coat and maternal plasma was performed using the iPLEX™ assay and MassARRAY® technology (Jurinke, C., Oeth, P., van den Boom, D., MALDI-TOF mass spectrometry: a versatile tool for high-performance DNA analysis. *Mol. Biotechnol.* 26, 147-164 (2004); and Oeth, P. et al., iPLEX™ Assay: Increased Plexing Efficiency and Flexibility for MassARRAY® System through single base primer extension with mass-modified Terminators. SEQUENOM Application Note (2005), both of which are hereby incorporated by reference). In brief, the target region surrounding the SNP is first amplified by PCR. Subsequently an oligonucleotide primer is annealed to the PCR product and is extended allele-specifically by a single nucleotide using a mixture of 4 terminator nucleotides and a DNA polymerase. The extension products are transferred to a miniaturized chip array and are analyzed by MALDI-TOF Mass Spectrometry. Determination of the molecular mass of extension products allows unambiguous identification of the SNP allele present in the sample. The peak area ratio of mass signals allows the estimation of the relative abundance of the alleles in a given sample. FIG. 6 provides an overview of the assay used for SNP analysis.

Clinical Samples

The total sample set consisted of 35 paired blood/plasma samples from pregnant Caucasian woman (nine 1st trimester; twelve 2nd trimester; fourteen 3rd trimester).

The subset of samples used for correlation of Y-chromosome frequency and paternally-inherited alleles in maternal plasma consisted of 19 samples of pregnant Caucasian woman carrying a male fetus.

DNA Extraction

DNA extraction was performed from 1 ml of maternal plasma using the Qiagen MinElute kit for fetal genotyping.

DNA extraction from frozen blood (minus plasma) was performed from 4 ml using Qiagen's PureGene kit for maternal genotyping.

Results

An assay targeting sequence differences in the Amelogenin region on the X and Y chromosome was used to assess the relative amount of fetal DNA extracted from plasma of pregnant woman carrying a male fetus. Details of the AMG assay are depicted in FIGS. 3A-3C. X and Y-specific sequences can be discriminated by sequence specific iPLEX extension products and their respective mass signals. The peak area ratio of the extension products allows estimation of the relative amount of fetal DNA, because the Y-specific sequences represent 50% of the total fetal DNA contribution.

Sixteen of nineteen (84%) plasma samples with a male fetus showed a Y-chromosome frequency of higher than 5%, indicating presence of at least 10% fetal DNA in the extracted DNA.

Figure 7:
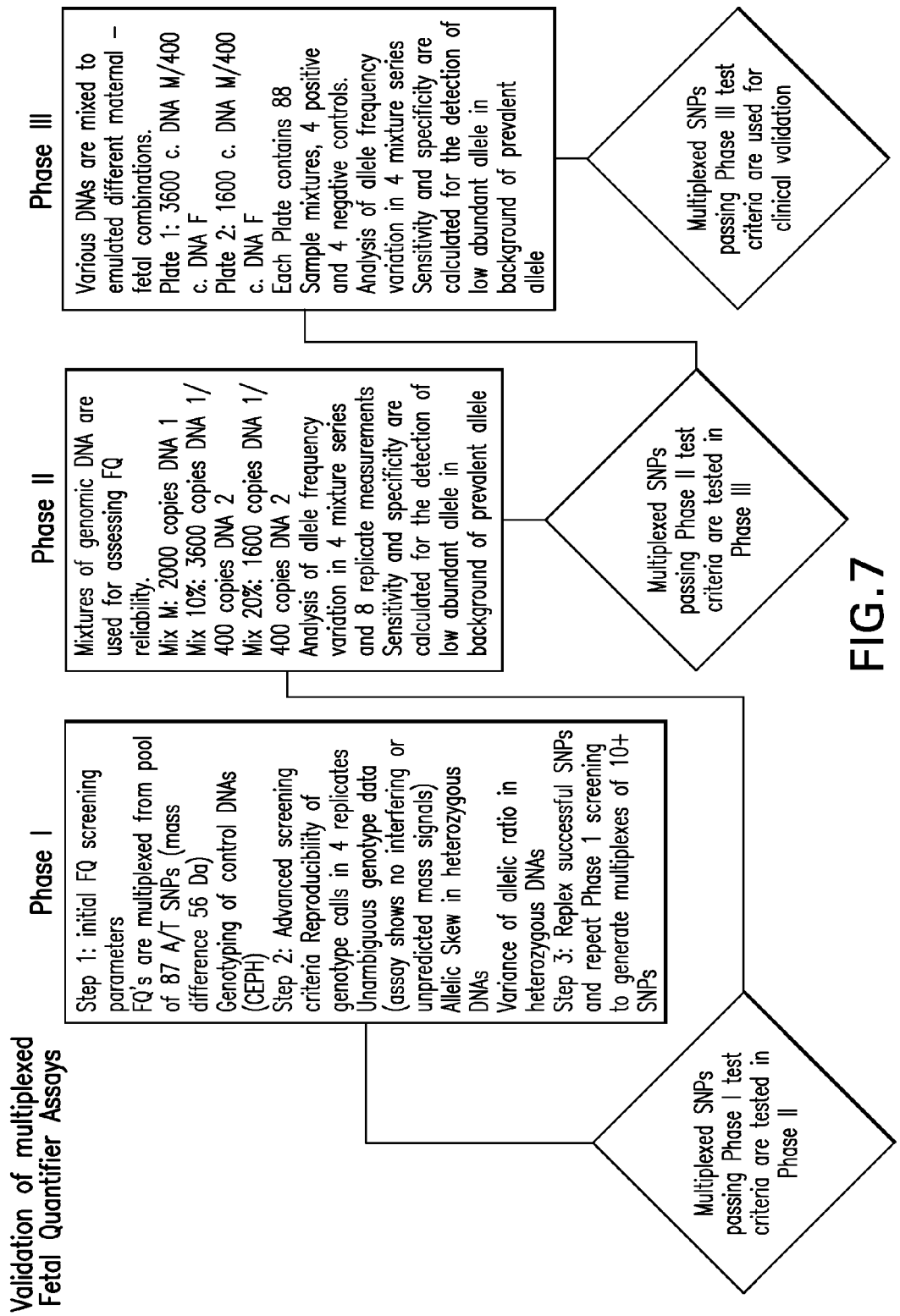
FIG. 7 depicts the validation scheme, performance criteria and model system used to qualify multiplex SNP assays for their utility in identifying the presence for fetal DNA.
Figure 8:
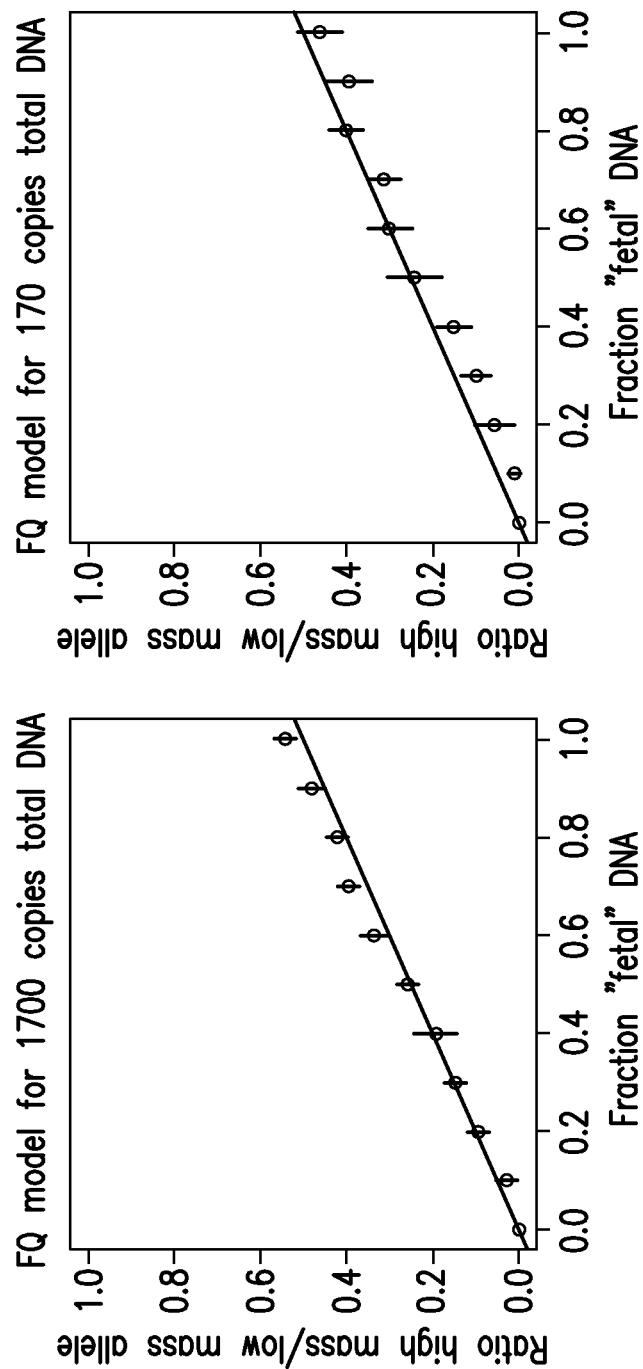
FIG. 8 depicts typical performance results for a qualified fetal identifier. Here the ability of the SNP assay to estimate the quantity of fetal DNA in the background of maternal DNA was verified for a total of 1700 copies and a total of 170 copies using genomic DNA mixtures. Note that the standard deviation of the estimate of fetal DNA increases due to the significant influence of the sampling error at low copy numbers
Figure 9:
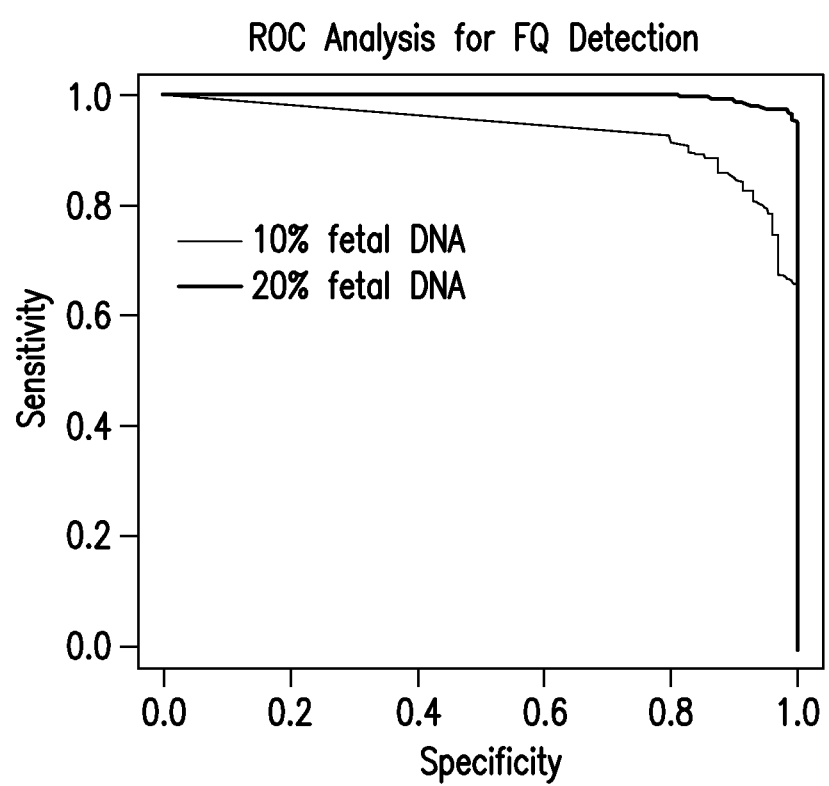
FIG. 9 shows the performance of multiplexed SNP assays (21 assays total) for detection of paternally-inherited alleles in a model system.

FIG. 8 depicts typical performance results for a qualified fetal identifier. Here the ability of the SNP assay to estimate the quantity of fetal DNA in the background of maternal DNA was verified for a total of 1700 copies and a total of 170 copies using genomic DNA mixtures. Note that the standard deviation of the estimate of fetal DNA increases due to the significant influence of the sampling error at low copy numbers Table 2 provides a list of SNPs that were multiplexed at 10+ plexing level and passed all phases of the validation shown in FIG. 7. Application of this assay panel to a model system for the detection of fetal DNA in maternal background showed that paternally-inherited fetal alleles can be detected with a sensitivity of 95% at 100% specificity if the sample preparation method can enrich the relative amount of fetal DNA to 20%. In Table 2, the minor allele frequency (MAF) for each SNP from different ethnic populations is provided. The ethnic populations are defined by the HapMap Project, where CEU represents individuals of Northern and Western Europe descent, HCB represents Han Chinese in Beijing, JAP represents Japanese in Tokyo, and YR1 represents the Yoruba in Ibadan, Nigeria.

TABLE 2

| SNP | MAF CEU | MAF HCB | MAF JAP | MAF YRI |
|---|---|---|---|---|
| rs11166512 | 0.43 | 0.41 | 0.50 | 0.49 |
| rs11184494 | 0.50 | 0.40 | 0.48 | 0.50 |
| rs11247894 | 0.43 | 0.39 | 0.32 | 0.44 |
| rs12089156 | 0.46 | 0.49 | 0.44 | 0.43 |
| rs12125888 | 0.40 | 0.43 | 0.48 | 0.43 |
| rs12136370 | 0.42 | 0.48 | 0.42 | 0.48 |
| rs12143315 | 0.40 | 0.42 | 0.42 | 0.42 |
| rs12759642 | 0.39 | 0.48 | 0.48 | 0.42 |
| rs156988 | 0.46 | 0.40 | 0.45 | 0.41 |
| rs2050927 | 0.44 | 0.50 | 0.41 | 0.49 |
| rs213624 | 0.48 | 0.44 | 0.40 | 0.34 |
| rs2454175 | 0.46 | 0.48 | 0.43 | 0.40 |
| rs4329520 | 0.45 | 0.43 | 0.40 | 0.44 |
| rs4487973 | 0.47 | 0.43 | 0.44 | 0.40 |
| rs454782 | 0.48 | 0.40 | 0.41 | 0.46 |
| rs4648888 | 0.33 | 0.30 | 0.33 | 0.46 |
| rs635364 | 0.49 | 0.40 | 0.46 | 0.43 |
| rs660279 | 0.41 | 0.49 | 0.50 | 0.39 |
| rs6687785 | 0.48 | 0.46 | 0.48 | 0.44 |
| rs7551188 | 0.46 | 0.49 | 0.45 | 0.46 |
| rs9431593 | 0.41 | 0.43 | 0.49 | 0.40 |

A multiplexed panel of 16 SNPs was analyzed with maf >0.3 in the same maternal plasma DNA extraction and established a baseline of maternal genotypes by analyzing DNA from PBMCs. Using the maternal genotype information, paternally-inherited alleles were identified in plasma samples and estimated the amount of fetal DNA from the peak area ratio of extension products representing paternally-inherited fetal alleles and maternal alleles.

The AMG XY frequency was then compared with the allele-frequency of paternally-inherited fetal alleles in informative SNPs. This comparison revealed that samples with a positive Y-frequency of 10% (used as a Limit-of-quantitation threshold) or more have significantly higher differences between maternally and paternally-inherited fetal allele-frequencies (p-value <0.001; Fishers' exact test). This data shows that Fetal Identifiers can be used as a non-gender specific approach for identification of the presence of fetal DNA. FIG. 8 exemplifies those results.

Example 3

Multiplex Schemes

The above described RhD, fetal identifier and sex test may be run simultaneously in various multiplex schemes. Exemplary multiplex schemes are provided in FIG. 10. For example, in the Scenario 1 assay, two multiplex reactions are run in parallel. In the MP1, the following reactions are performed: 10 Fetal Identifiers reactions, the RhD 4 reaction, the RhD 10 reaction and the SRY reaction. In the MP2, the following reactions are performed: 11 Fetal Identifiers reactions, the RhD 4 psi quantitative reaction, the RhD 5 reaction and the RhD 7 reaction. Other exemplary multiplex schemes are provided in FIG. 10, but are not intended to limit the scope of the invention.

The PCR primers and extend primers for MP1 and MP2 are provided below in Table 3. Lower case nucleotides in the extend primer sequence represent non-template nucleotides that are added as mass modifiers. Additional fetal identifiers which may be used as described herein are provided in Table 4.

TABLE 3

| Multiplex | Primer Name | Amplification primer | Amplification primer | Extend Primer sequence |
|---|---|---|---|---|
| MP1 | RhD-10-3r-i | ACGTTGGATGACGCTCATGACAGCAAAGTC (SEQ ID NO: 12) | ACGTTGGATGAACTCCATTTTCTCTGACTC (SEQ ID NO: 13) | gGTCTCCAATGTTCGCGCAGGCAC (SEQ ID NO: 15) |
| MP1 | RhD-4-3r-i | ACGTTGGATGCTGCCAAAGCCTCTACACG (SEQ ID NO: 1) | ACGTTGGATGTGGCAGACAAACTGGGTGTC (SEQ ID NO: 2) | GAACGGAGGATAAAGATCAGA (SEQ ID NO: 17) |
| MP1 | rs7551188 | ACGTTGGATGATCCCTGGTTCCTTCCTTAG (SEQ ID NO: 27) | ACGTTGGATGGAGCCTCTCAGTGTCTATAC (SEQ ID NO: 28) | GGACAGATTCTGGGAC (SEQ ID NO: 29) |
| MP1 | rs11247894 | ACGTTGGATGATCCTAGATAGCCCAAAGCC (SEQ ID NO: 30) | ACGTTGGATGGGAGGAAAGAGAAGATTGTG (SEQ ID NO: 31) | CCAAAGCCAAGAATTCA (SEQ ID NO: 32) |
| MP1 | rs6687785 | ACGTTGGATGATGCTGTAAAGAGCCTCAAC (SEQ ID NO: 33) | ACGTTGGATGTTCTCCTCTGACCTGCTTTC (SEQ ID NO: 34) | CCTCAACAGTACACTTAATC (SEQ ID NO: 35) |

TABLE 3-continued

| Multiplex | Primer Name | Amplification primer | Amplification primer | Extend Primer sequence |
|---|---|---|---|---|
| MP1 | rs4487973 | ACGTTGGATGTCAGAGAGTGACAAGACCTG (SEQ ID NO: 36) | ACGTTGGATGGAATGCATGCCAACTTAGGG (SEQ ID NO: 37) | cAGGTCACACAGTTAGGATT (SEQ ID NO: 38) |
| MP1 | rs4648888 | ACGTTGGATGCAGAGAGTCCCCTGTTATTG (SEQ ID NO: 39) | ACGTTGGATGTGCCCAGACCAGAGAGGTCA (SEQ ID NO: 40) | aTGGACCTTCGGAAAGGATA (SEQ ID NO: 41) |
| MP1 | rs12089156 | ACGTTGGATGGCTACATACTATGTGGTCTC (SEQ ID NO: 42) | ACGTTGGATGCCTGCTGGCAACAAATCTTC (SEQ ID NO: 43) | TACTATGTGGTCTCAACTATAT (SEQ ID NO: 44) |
| MP1 | rs2050927 | ACGTTGGATGTTCTAGCTTGCTTCTCCTCC (SEQ ID NO: 45) | ACGTTGGATGTTGGGTGCAGAGTAGTCATC (SEQ ID NO: 46) | TGCTTCTCCTCCATCATCCTTAGC (SEQ ID NO: 47) |
| MP1 | rs12125888 | ACGTTGGATGCAACATCCTGTACATCACTC (SEQ ID NO: 48) | ACGTTGGATGAGACAATTTCTGTCCTCTGG (SEQ ID NO: 49) | TACATGACTATCTCCTCCCTTAGGT (SEQ ID NO: 50) |
| MP1 | rs12143315 | ACGTTGGATGACAGGCATGAGCCATCTTAC (SEQ ID NO: 51) | ACGTTGGATGTGCCATTGGTACAGTCACTC (SEQ ID NO: 52) | CCATCTTACCCAGCCTCTTTCTTCAA (SEQ ID NO: 53) |
| MP1 | rs213624 | ACGTTGGATGTAGGTCAAGCCAAGGCCTC (SEQ ID NO: 54) | ACGTTGGATGTGTCCACCCAGGAGCAGCCA (SEQ ID NO: 55) | gGCCAAGGCCTCGGAGTCTGAACAGTT (SEQ ID NO: 56) |
| MP1 | SRY_5-ib | ACGTTGGATGAGCATCTAGGTAGGTCTTTG (SEQ ID NO: 24) | ACGTTGGATGAGCAACGGACCGCTACAG (SEQ ID NO: 25) | cGTTACCCGATTGTCCTAC (SEQ ID NO: 57) |
| MP2 | RhD-4-psi-3r-i | ACGTTGGATGGACTATCAGGGCTTGCCCCG (SEQ ID NO: 5) | ACGTTGGATGTGCGAACACGTAGATGTGAC (SEQ ID NO: 58) | cTGCAGACAGACTACCACATGAAC (SEQ ID NO: 18) |
| MP2 | RhD-5_3r-i | ACGTTGGATGAATCGAAAGGAAGAATGCCG (SEQ ID NO: 7) | ACGTTGGATGCTGAGATGGCTGTCACCACG (SEQ ID NO: 8) | ATGCCGTGTTCAACACCTACTATGCT (SEQ ID NO: 19) |
| MP2 | RhD-7-3r-i | ACGTTGGATGAGCTCCATCATGGGCTACAA (SEQ ID NO: 9) | ACGTTGGATGTTGCCGGCTCCGACGGTATC (SEQ ID NO: 10) | CTTGCTGGGTCTGCTTGGAGAGATCA (SEQ ID NO: 22) |
| MP2 | rs660279 | ACGTTGGATGTTTCAGCAACCACTCTGAGC (SEQ ID NO: 59) | ACGTTGGATGTGCCCGTAAGTAGGAGAGTG (SEQ ID NO: 60) | CTTGATGTGCTTCCCTG (SEQ ID NO: 61) |
| MP2 | rs635364 | ACGTTGGATGGAAATTTCTGGATTACTGGC (SEQ ID NO: 62) | ACGTTGGATGAGAGACTCCATTTGTTTGGG (SEQ ID NO: 63) | TGGATTACTGGCAAAGAC (SEQ ID NO: 64) |
| MP2 | rs9431593 | ACGTTGGATGTTGAGATCAGTGTCGGTTCC (SEQ ID NO: 65) | ACGTTGGATGGCCTCAGTAGTCACATAAGG (SEQ ID NO: 66) | TGTTCCTGACTCTCAAAAT (SEQ ID NO: 67) |
| MP2 | rs11166512 | ACGTTGGATGCTTCATCCACTATATCCACC (SEQ ID NO: 68) | ACGTTGGATGTGACCAGATGTTGGATTAG (SEQ ID NO: 69) | CCACTATATCCACCTTTTCT (SEQ ID NO: 70) |
| MP2 | rs4329520 | ACGTTGGATGGAAAGTTGTCGTGGTAGAGG (SEQ ID NO: 71) | ACGTTGGATGATGTCCACCTCCTGCTCCAC (SEQ ID NO: 72) | GCGTGGTTCTAGACTTATGC (SEQ ID NO: 73) |
| MP2 | rs454782 | ACGTTGGATGCTGTTAAGATGCCAACTCCC (SEQ ID NO: 74) | ACGTTGGATGCTGTCTTCCTCATTGCTCTG (SEQ ID NO: 75) | AACTCCCATATTAGTCCACAG (SEQ ID NO: 76) |
| MP2 | rs12136370 | ACGTTGGATGGAGTAGTTCTTTGCAGTAAGC (SEQ ID NO: 77) | ACGTTGGATGCTCCTGGAAACAGCAAAG (SEQ ID NO: 78) | gGCAGTAAGCTATTCTTGGGG (SEQ ID NO: 79) |
| MP2 | rs12759642 | ACGTTGGATGATTCTTCCTGGGACTCAGAC (SEQ ID NO: 80) | ACGTTGGATGGGAAATACCAGCAACCACAG (SEQ ID NO: 81) | caTCGGGATTCCCTGAACAAAA (SEQ ID NO: 82) |

TABLE 3-continued

| Multiplex | Primer Name | Amplification primer | Amplification primer | Extend Primer sequence |
|---|---|---|---|---|
| MP2 | rs11184494 | ACGTTGGATGAGCTGGCCAT GTTTATTTGAC (SEQ ID NO: 83) | ACGTTGGATGGCCAATCTAT GAAGAATTAC (SEQ ID NO: 84) | ATTTGACTTTCCTACTCCTTAAC (SEQ ID NO: 85) |
| MP2 | rs2454175 | ACGTTGGATGGGAATCAGAC CTGTAAACAC (SEQ ID NO: 86) | ACGTTGGATGGCCCAGCAGG ACACTTTTAT (SEQ ID NO: 87) | cCTTCAAGGATTGGAATTAGAGT (SEQ ID NO: 88) |
| MP2 | rs156988 | ACGTTGGATGAAAGCTCTGT GATGCGTCTC (SEQ ID NO: 89) | ACGTTGGATGGAAAGGGCTA TGTAAGGAGG (SEQ ID NO: 90) | tCGTCTCGGTCCTTCCTTTTCACTT (SEQ ID NO: 91) |

TABLE 4

| Multiplex | SNP_ID | Amplification primer | Amplification primer | Extend Primer sequence |
|---|---|---|---|---|
| W1 | rs10793675 | ACGTTGGATGAAGAGATGAG ACAGACTGGG (SEQ ID NO: 92) | ACGTTGGATGCTCTGTATTT ATAGCTTTC (SEQ ID NO: 93) | AACGGCTCAACAGTT (SEQ ID NO: 94) |
| W1 | rs1829309 | ACGTTGGATGATCTCTGAGT TGACACCACC (SEQ ID NO: 95) | ACGTTGGATGTTCCTAATCA GGAGAGACCG (SEQ ID NO: 96) | TTGCTTTGGGGAGCAG (SEQ ID NO: 97) |
| W1 | rs6602279 | ACGTTGGATGTTTCAGCAAC CACTCTGAGC (SEQ ID NO: 59) | ACGTTGGATGTGCCCGTAAG TAGGAGAGTG (SEQ ID NO: 60) | CTTGATGTGCTTCCCTG (SEQ ID NO: 61) |
| W1 | rs635364 | ACGTTGGATGGAAATTTCTG GATTACTGGC (SEQ ID NO: 62) | ACGTTGGATGAGAGACTCCA TTTGTTTGGG (SEQ ID NO: 63) | TGGATTACTGGCAAAGAC (SEQ ID NO: 64) |
| W1 | rs9431593 | ACGTTGGATGTTGAGATCAG TGTCGGTTCC (SEQ ID NO: 65) | ACGTTGGATGGCCTCAGTAG TCACATAAGG (SEQ ID NO: 66) | TGTTCCTGACTCTCAAAAT (SEQ ID NO: 67) |
| W1 | rs11166512 | ACGTTGGATGCTTCATCCAC TATATCCACC (SEQ ID NO: 68) | ACGTTGGATGTGACCAGATG TTTGGATTAG (SEQ ID NO: 69) | CCACTATATCCACCTTTTCT (SEQ ID NO: 70) |
| W1 | rs4329520 | ACGTTGGATGGAAAGTTGTC GTGGTAGAGG (SEQ ID NO: 71) | ACGTTGGATGATGTCCACCT CCTGCTCCAC (SEQ ID NO: 72) | GCGTGGTTCTAGACTTATGC (SEQ ID NO: 73) |
| W1 | rs454782 | ACGTTGGATGCTGTTAAGAT GCCAACTCCC (SEQ ID NO: 74) | ACGTTGGATGCTGTCTTCCT CATTGCTCTG (SEQ ID NO: 75) | AACTCCCATATTAGTCCACAG (SEQ ID NO: 76) |
| W1 | rs12136370 | ACGTTGGATGGAGTAGTTCT TTGCAGTAAGC (SEQ ID NO: 77) | ACGTTGGATGCTCCTGGAAA ACAGCAAAG (SEQ ID NO: 76) | gGCAGTAAGCTATTCTTGGGG (SEQ ID NO: 79) |
| W1 | rs12759642 | ACGTTGGATGATTCTTCCTG GGACTCAGAC (SEQ ID NO: 80) | ACGTTGGATGGGAAATACCA GCAACCACAG (SEQ ID NO: 81) | caTCGGGATTCCCTGAACAAAA (SEQ ID NO: 82) |
| W1 | rs11184494 | ACGTTGGATGAGCTGGCCAT GTTTATTTGAC (SEQ ID NO: 83) | ACGTTGGATGGCCAATCTAT GAAGAATTAC (SEQ ID NO: 84) | ATTTGACTTTCCTACTCCTTAAC (SEQ ID NO: 85) |
| W1 | rs2454175 | ACGTTGGATGGGAATCAGAC CTGTAAACAC (SEQ ID NO: 86) | ACGTTGGATGGCCCAGCAGG ACACTTTTAT (SEQ ID NO: 87) | cCTTCAAGGATTGGAATTAGAGT (SEQ ID NO: 88) |
| W1 | rs1452628 | ACGTTGGATGGCTTGTGCTT TGTTGTGTGG (SEQ ID NO: 98) | ACGTTGGATGGGTCAAGCAA AGGCTTCAAG (SEQ ID NO: 99) | acatAGTTATTCCTAGGGCTTCTC (SEQ ID NO: 100) |
| W1 | rs156988 | ACGTTGGATGAAAGCTCTGT GATGCGTCTC (SEQ ID NO: 89) | ACGTTGGATGGAAAGGGCTA TGTAAGGAGG (SEQ ID NO: 90) | tCGTCTCGGTCCTTCCTTTTCACTT (SEQ ID NO: 91) |

TABLE 4-continued

| Multiplex | SNP_ID | Amplification primer | Amplification primer | Extend Primer sequence |
|---|---|---|---|---|
| W1 | rs4570430 | ACGTTGGATGACCCGAGCCA<br>ATCAGGTATC<br>(SEQ ID NO: 101) | ACGTTGGATGGCACATGGAG<br>ATGAATGGTC<br>(SEQ ID NO: 102) | GGTATCATAAGATACCTATGATGTC<br>(SEQ ID NO: 103) |
| W1 | rs12062414 | ACGTTGGATGTGCGTCAACC<br>TTTCCAGTTC<br>(SEQ ID NO: 104) | ACGTTGGATGGGAAAGTCCT<br>CGACTGTTTG<br>(SEQ ID NO: 105) | ggaaTTTCCAGTTCTATTCCAGCCTC<br>(SEQ ID NO: 106) |
| W1 | rs7545381 | ACGTTGGATGCCAGTCAAGC<br>TAAGGACAAA<br>(SEQ ID NO: 107) | ACGTTGGATGGTGAGCACAA<br>CTGTGTTCTA<br>(SEQ ID NO: 108) | tccCTGAATGACAAAAGGGGAAGATA<br>(SEQ ID NO: 109) |
| W1 | rs6427673 | ACGTTGGATGGGACTAAAAC<br>AGGGCCAAAC<br>(SEQ ID NO: 110) | ACGTTGGATGGTCTCTCTAG<br>TACTAGTAAC<br>(SEQ ID NO: 111) | ccctcGCCAAACTTAGACCAAGGACAAC<br>(SEQ ID NO: 112) |
| W1 | rs10802761 | ACGTTGGATGTCTTCTAAAA<br>TGTAGTTATG<br>(SEQ ID NO: 113) | ACGTTGGATGGGATGAGGTT<br>TTGACTAAGC<br>(SEQ ID NO: 114) | AGTTATGAAATAAGTTTTATTCATTTAC<br>(SEQ ID NO: 115) |
| W2 | rs642449 | ACGTTGGATGCCAAAAAACC<br>ATGCCCTCTG<br>(SEQ ID NO: 116) | ACGTTGGATGAGATTGCCTC<br>TCCATGTGAC<br>(SEQ ID NO: 117) | CCTCTGCCTCCCCTA<br>(SEQ ID NO: 118) |
| W2 | rs4839419 | ACGTTGGATGCTGCCGCATC<br>CCTTCACAA<br>(SEQ ID NO: 119) | ACGTTGGATGATGTGTTTGT<br>GGCCACTTCC<br>(SEQ ID NO: 120) | CCTTCACAAAGCCGA<br>(SEQ ID NO: 121) |
| W2 | rs9324198 | ACGTTGGATGAAAGGCCTAC<br>TGTTTGCTGG<br>(SEQ ID NO: 122) | ACGTTGGATGCAAAATATGT<br>GTGAATCAGC<br>(SEQ ID NO: 123) | cGTTTGCTGGAAGCCT<br>(SEQ ID NO: 124) |
| W2 | rs1192619 | ACGTTGGATGGCTCAACTCT<br>GAACCAATCG<br>(SEQ ID NO: 125) | ACGTTGGATGCCAGGAATGG<br>GCATGTGTTC<br>(SEQ ID NO: 126) | TGGCCAGAAGAAGGAG<br>(SEQ ID NO: 127) |
| W2 | rs4657868 | ACGTTGGATGCTAACCAGGA<br>AAAGACACCC<br>(SEQ ID NO: 128) | ACGTTGGATGCTAGCGTACC<br>CAATGGAATC<br>(SEQ ID NO: 129) | AGACACCCCCATACATTA<br>(SEQ ID NO: 130) |
| W2 | rs6426873 | ACGTTGGATGAAATCAGGG<br>CTGCCTTCTC<br>(SEQ ID NO: 131) | ACGTTGGATGAAGTGCTAGG<br>GTTACAGGTG<br>(SEQ ID NO: 132) | cccCTGCCTTCTCTTCCAA<br>(SEQ ID NO: 133) |
| W2 | rs438981 | ACGTTGGATGTGTGCAAATT<br>GGCTAACAT<br>(SEQ ID NO: 134) | ACGTTGGATGGAACATTGGT<br>ATTTAAACTC<br>(SEQ ID NO: 135) | ATGGACCACAAAAAACTTA<br>(SEQ ID NO: 136) |
| W2 | rs12125888 | ACGTTGGATGAGACAATTTC<br>TGTCCTCTGG<br>(SEQ ID NO: 49) | ACGTTGGATGCAACATCCTG<br>TACATCACTC<br>(SEQ ID NO: 48) | TCTGTCCTCTGGTATCCTCT<br>(SEQ ID NO: 137) |
| W2 | rs3128688 | ACGTTGGATGATCAAGAGGA<br>AAATGGACAG<br>(SEQ ID NO: 138) | ACGTTGGATGGATTTACTCA<br>ACTCTCTGGG<br>(SEQ ID NO: 139) | cAAAATGGACAGAAGTTGAA<br>(SEQ ID NO: 140) |
| W2 | rs4987351 | ACGTTGGATGGTGCATGGGC<br>TCATCTAGAC<br>(SEQ ID NO: 141) | ACGTTGGATGCCAAACAGGG<br>CCAATGGTAG<br>(SEQ ID NO: 142) | gCATCTAGACACATTTTGTGC<br>(SEQ ID NO: 143) |
| W2 | rs6692911 | ACGTTGGATGCTATTCCCTC<br>CTCAAAGAGC<br>(SEQ ID NO: 144) | ACGTTGGATGATTAAGATGG<br>GTAGTTAAG<br>(SEQ ID NO: 145) | tccAAGAGCATTTTTCCTCTTC<br>(SEQ ID NO: 146) |
| W2 | rs6684679 | ACGTTGGATGTATGTTACTT<br>GCCTTGGCCC<br>(SEQ ID NO: 147) | ACGTTGGATGTCTTAAGGTG<br>TCTCCCTCTG<br>(SEQ ID NO: 148) | ggaCCACTGAGGAGATACACTA<br>(SEQ ID NO: 149) |
| W2 | rs4320829 | ACGTTGGATGGGTTCTATGG<br>CTTTGGTGAG<br>(SEQ ID NO: 150) | ACGTTGGATGTGCTAGACAC<br>TTTAACTGCC<br>(SEQ ID NO: 151) | ggtcACCTCTTTTCATAACAGGA<br>(SEQ ID NO: 152) |
| W2 | rs4658481 | ACGTTGGATGCTGCTAAGCA<br>TGAGAGAAAG<br>(SEQ ID NO: 153) | ACGTTGGATGGTGGTAGAAA<br>CAAATGTCAGC<br>(SEQ ID NO: 154) | atacGCATGAGAGAAAGGGAAAG<br>(SEQ ID NO: 155) |

TABLE 4-continued

| Multiplex | SNP_ID | Amplification primer | Amplification primer | Extend Primer sequence |
|---|---|---|---|---|
| W2 | rs3768458 | ACGTTGGATGCCAAATGTCT TAGTTACAAAG (SEQ ID NO: 156) | ACGTTGGATGGAGTTTATGT AATGTCAAC (SEQ ID NO: 157) | CTTAGTTACAAAGAAAATTGTGAG (SEQ ID NO: 158) |
| W2 | rs860954 | ACGTTGGATGTAGCCTTTAG TCTTGATGCC (SEQ ID NO: 159) | ACGTTGGATGCCATTCTTGT ATGTTTTGTC (SEQ ID NO: 160) | TCTTGATGCCTTACAAAATAAATAT (SEQ ID NO: 161) |
| W2 | rs10453878 | ACGTTGGATGGAGGAGCTAA CAAGTAGGAC (SEQ ID NO: 162) | ACGTTGGATGGGGATATGAA TTACAACAGAG (SEQ ID NO: 163) | AAACAAATCCTCCTTTCTTTTAATTC (SEQ ID NO: 164) |
| W2 | rs10753912 | ACGTTGGATGGAGATTATAT GTCTCTTTAA (SEQ ID NO: 165) | ACGTTGGATGATTCTTCTAA CTTTTAGGC (SEQ ID NO: 166) | GAGATTATATGTCTCTTTAATATTGTC (SEQ ID NO: 167) |
| W2 | rs1637944 | ACGTTGGATGCTAATGCCTC CTTTTCTTCC (SEQ ID NO: 168) | ACGTTGGATGAATAGCAAAC AACAGGTGGG (SEQ ID NO: 169) | cccccATATCATTTGCAATTGCATGGTT (SEQ ID NO: 170) |
| W2 | rs4839282 | ACGTTGGATGGAATCCTGGC AGCTCATTAG (SEQ ID NO: 171) | ACGTTGGATGTGGGTTCACA TGAGTCTTGC (SEQ ID NO: 172) | gatgTCTCTTAAAGAGCAAAAAGCTAAG (SEQ ID NO: 173) |

Figure 10:
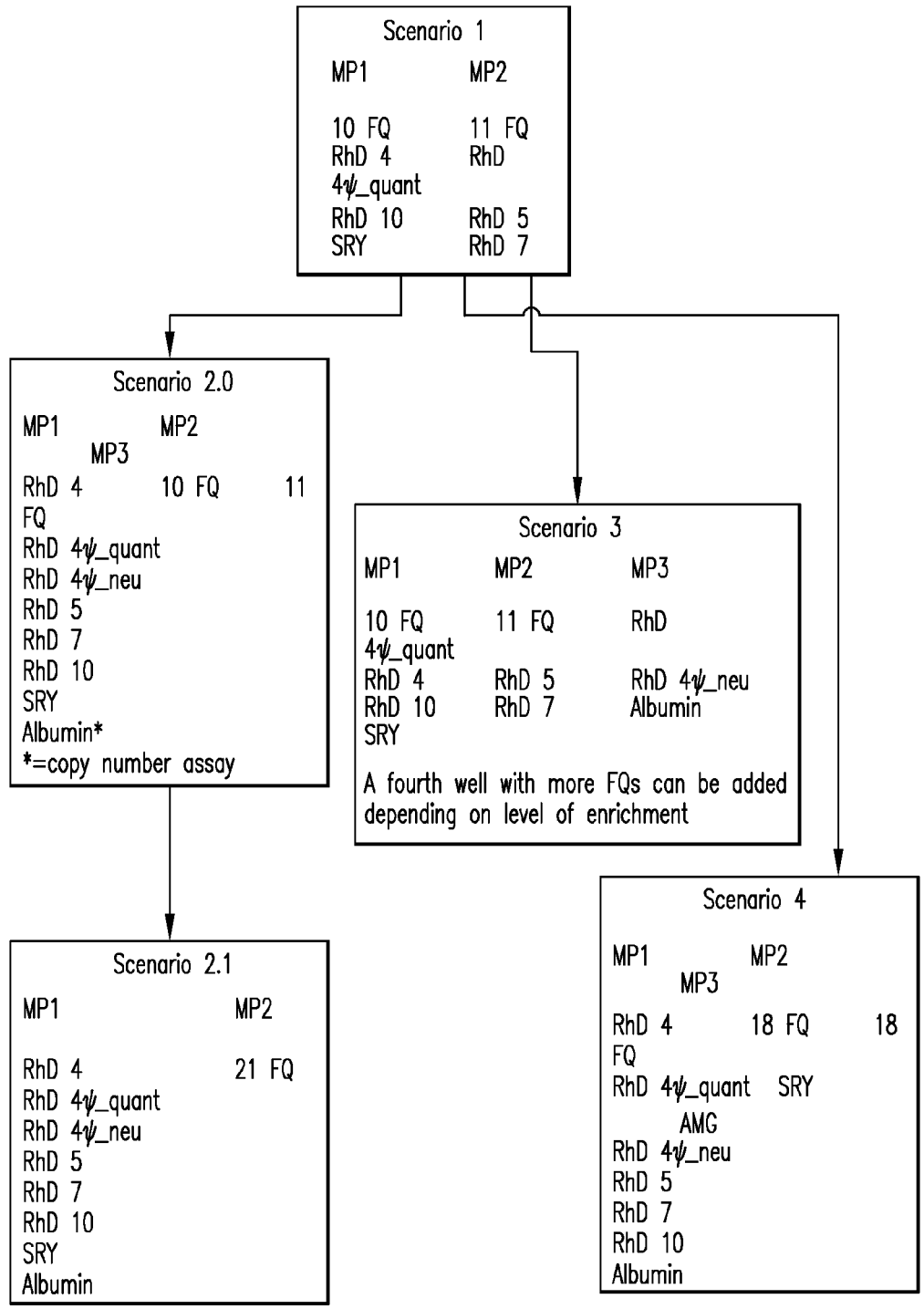
FIG. 10 (provided in duplicate) shows different multiplexed assay schemes of the invention.

Multiplex scheme 3 in FIG. 10 includes an albumin assay which may be performed to determine total copy number of DNA molecules for the human serum albumin gene. The albumin assay is useful to measure how much DNA is loaded into a particular reaction. It acts as an internal control and a guide to the likelihood of success for a particular PCR reaction. For example, if only 400 copies of ALB are measured then the probability of detecting any fetal DNA is very low. Primers for the Albumin assay are provided in FIG. 4.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, yet these modifications and improvements are within the scope and spirit of the invention.

The invention illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the invention claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" is about 1, about 2 and about 3). For example, a weight of "about 100 grams" can include weights between 90 grams and 110 grams. Thus, it should be understood that although the present invention has been specifically disclosed by representative embodiments and optional features, modification and variation of the concepts herein disclosed may be resorted to by those skilled in the art, and such modifications and variations are considered within the scope of this invention.

Embodiments of the invention are set forth in the claims that follow.

What is claimed is:

1. A method for determining the relative amount of fetal nucleic acid in a maternal plasma sample, comprising:
   (a) amplifying at least 10 polymorphic sites in nucleic acid obtained from a maternal plasma sample, which polymorphic sites comprise single nucleotide polymorphisms with a minor allele frequency of greater than 0.3 and are selected from the group consisting of: rs7551188, rs11247894, rs6687785, rs4487973, rs4648888, rs12089156, rs2050927, rs12125888, rs12143315, rs213624, rs660279, rs635364, rs9431593, rs11166512, rs4329520, rs454782, rs12136370, rs12759642, rs11184494, rs2454175, rs156988, rs10793675, rs1829309, rs1452628, rs4570430, rs12062414, rs7545381, rs6427673, rs10802761, rs642449, rs4839419, rs9324198, rs1192619, rs4657868, rs6426873, rs438981, rs3128688, rs4987351, rs6692911, rs6684679, rs4320829, rs4658481, rs3768458, rs860954, rs10453878, rs10753912, rs1637944 and rs4839282;
   (b) quantifying the relative amount of the alleles at said at least 10 polymorphic sites; and
   (c) expressing the relative amounts of fetal and maternal alleles as a ratio, wherein the ratio indicates the relative amount of fetal nucleic acid present in the maternal sample.

2. The method of claim 1, wherein said at least 10 polymorphic sites are selected from the group consisting of rs7551188, rs11247894, rs6687785, rs4487973, rs4648888, rs12089156, rs2050927, rs12125888, rs12143315, rs213624, rs660279, rs635364, rs9431593, rs11166512, rs4329520, rs454782, rs12136370, rs12759642, rs11184494, rs2454175 and rs156988.

* * * * *

SEQUENCE LISTING

<160> NUMBER OF SEQ ID NOS: 241

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
acgttggatg ctgccaaagc ctctacacg                                                29

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acgttggatg tggcagacaa actgggtgtc                                               30

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acgttggatg agaacggagg ataaagatca gac                                           33

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acgttggatg agccagcatg gcagacaaac tg                                            32

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acgttggatg gactatcagg gcttgccccg                                               30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acgttggatg tgcgaacacg tagatgtgca                                               30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acgttggatg aatcgaaagg aagaatgccg                                      30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acgttggatg ctgagatggc tgtcaccacg                                      30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acgttggatg agctccatca tgggctacaa                                      30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acgttggatg ttgccggctc cgacggtatc                                      30

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acgttggatg agctccatca tgggctacaa c                                    31

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acgttggatg acgctcatga cagcaaagtc                                      30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acgttggatg aactccattt tctctgactc                                      30

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acgttggatg actccatttt ctctgactc                               29

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggtctccaat gttcgcgcag gcac                                    24

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggataaagat cagacagcaa c                                       21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaacggagga taaagatcag a                                       21

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctgcagacag actaccacat gaac                                    24

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atgccgtgtt caacacctac tatgct                                  26

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gatggctgtc accacgctga ctgcta                                        26

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttgtcaccac gctgactgct a                                             21

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cttgctgggt ctgcttggag agatca                                        26

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gttacccgat tgtcctac                                                 18

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
acgttggatg agcatctagg taggtctttg                                    30

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acgttggatg agcaacggga ccgctacag                                     29

<210> SEQ ID NO 26
<211> LENGTH: 10

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
acgttggatg                                                             10

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
acgttggatg atccctggtt ccttccttag                                       30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acgttggatg gagcctctca gtgtctatac                                       30

<210> SEQ ID NO 29
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggacagattc tgggac                                                      16

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acgttggatg atcctagata gcccaaagcc                                       30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acgttggatg ggaggaaaga gaagattgtg                                       30

<210> SEQ ID NO 32
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 32
ccaaagccaa gaattca                                                        17

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acgttggatg atgctgtaaa gagcctcaac                                          30

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
acgttggatg ttctcctctg acctgctttc                                          30

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cctcaacagt acacttaatc                                                     20

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
acgttggatg tcagagagtg acaagacctg                                          30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acgttggatg gaatgcatgc caacttaggg                                          30

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 38
caggtcacac agttaggatt                                                     20

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acgttggatg cagagagtcc cctgttattg                                          30

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
acgttggatg tgcccagacc agagaggtca                                          30

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
atggaccttc ggaaaggata                                                     20

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
acgttggatg gctacatact atgtggtctc                                          30

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
acgttggatg cctgctggca acaaatcttc                                          30

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 44
tactatgtgg tctcaactat at                                              22

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
acgttggatg ttctagcttg cttctcctcc                                      30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
acgttggatg ttgggtgcag agtagtcatc                                      30

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgcttctcct ccatcatcct tagc                                            24

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
acgttggatg caacatcctg tacatcactc                                      30

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
acgttggatg agacaatttc tgtcctctgg                                      30

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
```

```
tacatgacta tctcctccct taggt                                          25
```

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51

```
acgttggatg acaggcatga gccatcttac                                     30
```

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52

```
acgttggatg tgccattggt acagtcactc                                     30
```

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53

```
ccatcttacc cagcctcttt cttcaa                                         26
```

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54

```
acgttggatg taggtcaagc caaggcctc                                      29
```

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55

```
acgttggatg tgtccaccca ggagcagcca                                     30
```

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56

```
ggccaaggcc tcggagtctg aacagtt                                        27
```

```
<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cgttacccga ttgtcctac                                                    19

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
acgttggatg tgcgaacacg tagatgtgac                                        30

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
acgttggatg tttcagcaac cactctgagc                                        30

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
acgttggatg tgcccgtaag taggagagtg                                        30

<210> SEQ ID NO 61
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cttgatgtgc ttccctg                                                      17

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
acgttggatg gaaatttctg gattactggc                                        30

<210> SEQ ID NO 63
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
acgttggatg agagactcca tttgtttggg                                           30

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tggattactg gcaaagac                                                        18

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
acgttggatg ttgagatcag tgtcggttcc                                           30

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
acgttggatg gcctcagtag tcacataagg                                           30

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tgttcctgac tctcaaaat                                                       19

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
acgttggatg cttcatccac tatatccacc                                           30

<210> SEQ ID NO 69
<211> LENGTH: 29
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 69
acgttggatg tgaccagatg ttggattag                                      29

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ccactatatc caccttttct                                                20

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
acgttggatg gaaagttgtc gtggtagagg                                     30

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
acgttggatg atgtccacct cctgctccac                                     30

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gcgtggttct agacttatgc                                                20

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
acgttggatg ctgttaagat gccaactccc                                     30

<210> SEQ ID NO 75
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 75
acgttggatg ctgtcttcct cattgctctg                                         30

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
aactcccata ttagtccaca g                                                  21

<210> SEQ ID NO 77
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
acgttggatg gagtagttct ttgcagtaag c                                       31

<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
acgttggatg ctcctggaaa acagcaaaag                                         30

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ggcagtaagc tattcttggg g                                                  21

<210> SEQ ID NO 80
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
acgttggatg attcttcctg ggactcagac                                         30

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 81
acgttggatg ggaaatacca gcaaccacag                                    30

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
catcgggatt ccctgaacaa aa                                            22

<210> SEQ ID NO 83
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
acgttggatg agctggccat gtttatttga c                                  31

<210> SEQ ID NO 84
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
acgttggatg gccaatctat gaagaattac                                    30

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
atttgacttt cctactcctt aac                                           23

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
acgttggatg ggaatcagac ctgtaaacac                                    30

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
acgttggatg gcccagcagg acacttttat                                           30

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ccttcaagga ttggaattag agt                                                  23

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
acgttggatg aaagctctgt gatgcgtctc                                           30

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
acgttggatg gaaagggcta tgtaaggagg                                           30

<210> SEQ ID NO 91
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
tcgtctcggt ccttcctttt cactt                                                25

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
acgttggatg aagagatgag acagactggg                                           30

<210> SEQ ID NO 93
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
acgttggatg ctctgtattt atagctttc                                            29

<210> SEQ ID NO 94
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
aacggctcaa cagtt                                                          15

<210> SEQ ID NO 95
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
acgttggatg atctctgagt tgacaccacc                                          30

<210> SEQ ID NO 96
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
acgttggatg ttcctaatca ggagagaccg                                          30

<210> SEQ ID NO 97
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ttgctttggg gagcag                                                         16

<210> SEQ ID NO 98
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
acgttggatg gcttgtgctt tgttgtgtgg                                          30

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
acgttggatg ggtcaagcaa aggcttcaag                                          30

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
acatagttat tcctagggct tctc                                           24

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
acgttggatg acccgagcca atcaggtatc                                     30

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
acgttggatg gcacatggag atgaatggtc                                     30

<210> SEQ ID NO 103
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ggtatcataa gataccnatg atgtc                                          25

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
acgttggatg tgcgtcaacc tttccagttc                                     30

<210> SEQ ID NO 105
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
acgttggatg ggaaagtcct cgactgtttg                                     30

<210> SEQ ID NO 106
<211> LENGTH: 26

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ggaatttcca gttctattcc agcctc                                          26

<210> SEQ ID NO 107
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
acgttggatg ccagtcaagc taaggacaaa                                      30

<210> SEQ ID NO 108
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
acgttggatg gtgagcacaa ctgtgttcta                                      30

<210> SEQ ID NO 109
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
tccctgaatg acaaaagggg aagata                                          26

<210> SEQ ID NO 110
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
acgttggatg ggactaaaac agggccaaac                                      30

<210> SEQ ID NO 111
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
acgttggatg gtctctctag tactagtaac                                      30

<210> SEQ ID NO 112
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 112
ccctcgccaa acttagacca aggacaac                                          28

<210> SEQ ID NO 113
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
acgttggatg tcttctaaaa tgtagttatg                                        30

<210> SEQ ID NO 114
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
acgttggatg ggatgaggtt ttgactaagc                                        30

<210> SEQ ID NO 115
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
agttatgaaa taagttttat tcatttac                                          28

<210> SEQ ID NO 116
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
acgttggatg ccaaaaaacc atgccctctg                                        30

<210> SEQ ID NO 117
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
acgttggatg agattgcctc tccatgtgac                                        30

<210> SEQ ID NO 118
<211> LENGTH: 15
<212> TYPE: DNA
<213> ORGANISM: Artificial Sequence
<220> FEATURE:
<223> OTHER INFORMATION: Description of Artificial Sequence: Synthetic
```

-continued

```
primer

<400> SEQUENCE: 118
cctctgcctc cccta                                                        15

<210> SEQ ID NO 119
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
acgttggatg ctgccgcatc ccttcacaa                                         29

<210> SEQ ID NO 120
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
acgttggatg atgtgtttgt ggccacttcc                                        30

<210> SEQ ID NO 121
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ccttcacaaa gccga                                                        15

<210> SEQ ID NO 122
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
acgttggatg aaaggcctac tgtttgctgg                                        30

<210> SEQ ID NO 123
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
acgttggatg caaaatatgt gtgaatcagc                                        30

<210> SEQ ID NO 124
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 124
cgtttgctgg aagcct                                                        16

<210> SEQ ID NO 125
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
acgttggatg gctcaactct gaaccaatcg                                         30

<210> SEQ ID NO 126
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
acgttggatg ccaggaatgg gcatgtgttc                                         30

<210> SEQ ID NO 127
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
tggccagaag aaggag                                                        16

<210> SEQ ID NO 128
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
acgttggatg ctaaccagga aaagacaccc                                         30

<210> SEQ ID NO 129
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
acgttggatg ctagcgtacc caatggaatc                                         30

<210> SEQ ID NO 130
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
agacaccccc atacatta                                                        18

<210> SEQ ID NO 131
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
acgttggatg taaatcaggg ctgccttctc                                           30

<210> SEQ ID NO 132
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
acgttggatg aagtgctagg gttacaggtg                                           30

<210> SEQ ID NO 133
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
cccctgcctt ctcttccaa                                                       19

<210> SEQ ID NO 134
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
acgttggatg tgtgcaaatt ggctaacat                                            29

<210> SEQ ID NO 135
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
acgttggatg gaacattggt atttaaactc                                           30

<210> SEQ ID NO 136
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
atggaccaca aaaaactta                                                       19

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
tctgtcctct ggtatcctct                                              20

<210> SEQ ID NO 138
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
acgttggatg atcaagagga aaatggacag                                   30

<210> SEQ ID NO 139
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
acgttggatg gatttactca actctctggg                                   30

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
caaaatggac agaagttgaa                                              20

<210> SEQ ID NO 141
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
acgttggatg gtgcatgggc tcatctagac                                   30

<210> SEQ ID NO 142
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
acgttggatg ccaaacaggg ccaatggtag                                   30

<210> SEQ ID NO 143

<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 143
gcatctagac acattttgtg c  21

<210> SEQ ID NO 144
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 144
acgttggatg ctattccctc ctcaaagagc  30

<210> SEQ ID NO 145
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 145
acgttggatg attaagatgg gtagttaag  29

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 146
tccaagagca ttttcctct tc  22

<210> SEQ ID NO 147
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 147
acgttggatg tatgttactt gccttggccc  30

<210> SEQ ID NO 148
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 148
acgttggatg tcttaaggtg tctccctctg  30

<210> SEQ ID NO 149
<211> LENGTH: 22
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 149
ggaccactga ggagatacac ta                                            22

<210> SEQ ID NO 150
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
acgttggatg ggttctatgg ctttggtgag                                    30

<210> SEQ ID NO 151
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
acgttggatg tgctagacac tttaactgcc                                    30

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
ggtcacctct tttcataaca gga                                           23

<210> SEQ ID NO 153
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
acgttggatg ctgctaagca tgagagaaag                                    30

<210> SEQ ID NO 154
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
acgttggatg gtggtagaaa caaatgtcag c                                  31

<210> SEQ ID NO 155
<211> LENGTH: 23
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 155
atacgcatga gagaaaggga aag                                            23

<210> SEQ ID NO 156
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
acgttggatg ccaaatgtct tagttacaaa g                                   31

<210> SEQ ID NO 157
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
acgttggatg gagtttatgt aatgtcaac                                      29

<210> SEQ ID NO 158
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
cttagttaca aagaaaattg tgag                                           24

<210> SEQ ID NO 159
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
acgttggatg tagcctttag tcttgatgcc                                     30

<210> SEQ ID NO 160
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
acgttggatg ccattcttgt atgttttgtc                                     30

<210> SEQ ID NO 161
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 161
tcttgatgcc ttacaaaata aatat                                    25

<210> SEQ ID NO 162
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
acgttggatg gaggagctaa caagtaggac                               30

<210> SEQ ID NO 163
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
acgttggatg gggatatgaa ttacaacaga g                             31

<210> SEQ ID NO 164
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
aaacaaatcc tcctttcttt taattc                                   26

<210> SEQ ID NO 165
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
acgttggatg gagattatat gtctctttaa                               30

<210> SEQ ID NO 166
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
acgttggatg attcttctaa cttttaggc                                29

<210> SEQ ID NO 167
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
gagattatat gtctctttaa tattgtc                                              27

<210> SEQ ID NO 168
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
acgttggatg ctaatgcctc cttttcttcc                                           30

<210> SEQ ID NO 169
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
acgttggatg aatagcaaac aacaggtggg                                           30

<210> SEQ ID NO 170
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
cccccatatc atttgcaatt gcatggtt                                             28

<210> SEQ ID NO 171
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
acgttggatg gaatcctggc agctcattag                                           30

<210> SEQ ID NO 172
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
acgttggatg tgggttcaca tgagtcttgc                                           30

<210> SEQ ID NO 173
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
gatgtctctt aaagagcaaa aagctaag                                             28

<210> SEQ ID NO 174
<211> LENGTH: 359
<212> TYPE: DNA
<213> ORGANISM: Homo sapiens

<400> SEQUENCE: 174

```
gtaagctctg aacaccagtc tcatggcttc aagtcacacc tcctaagtga agctctgaac        60
tttctccaag gactatcagg gcttgccccg ggcagaggat gccgacactc actgctctta       120
ctgggtttta ttgcagacag actaccacat gaacatgatg cacatctacg tgttcgcagc       180
ctattttggg ctgtctgtgg cctggtgcct gccaaagcct ctacccgagg gaacggagga       240
taaagatcag acagcaacga tacccagttt gtctgccatg ctgggtaagg acaaggtggg       300
gtgagtggtc tcctacttgg gctgagcaga atggctcaga aaaggctctg gctgaaaaa       359
```

<210> SEQ ID NO 175
<211> LENGTH: 360
<212> TYPE: DNA
<213> ORGANISM: Homo sapiens

<400> SEQUENCE: 175

```
gtaagctctg aacaccagtc tcgtggcttc aagtcacacc tcctaagtga agctctgaac        60
tttctccaag gaccatcagg gctttcccct gggcagagga tgccgacact cactgctctt       120
actgggtttt attgcagaca gactaccaca tgaacctgag gcacttctac gtgttcgcag       180
cctattttgg gctgactgtg gcctggtgcc tgccaaagcc tctacccaag gaacggagg        240 ataatgatca gagagcaacg atacccagtt tgtctgccat gctgggtaag gacaaggtgg       300
ggtgagtggt ctcatacttg ggctgagcag aatggctcag aaaaggctct ggctgaaaaa       360
```

<210> SEQ ID NO 176
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176

```
ttactgggtt ttattgcaga cagactacca catgaac                                 37
```

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177

```
gataaagatc agacagcaac                                                    20
```

<210> SEQ ID NO 178
<211> LENGTH: 240
<212> TYPE: DNA
<213> ORGANISM: Homo sapiens

<400> SEQUENCE: 178

```
tttggagcag gagtgtgatt ctggccaacc accctctctg gccccaggc gccctcttct        60 tgtggatgtt ctggccaagt ttcaactctg ctctgctgag aagtccaatc gaaaggaaga      120
atgccgtgtt caacacctac tatgctgtag cagtcagcgt ggtgacagcc atctcagggt      180
```

```
catccttggc tcaccccaa gggaagatca gcaaggtgag cagggcgctg cccttgggca        240
```

<210> SEQ ID NO 179
<211> LENGTH: 240
<212> TYPE: DNA
<213> ORGANISM: Homo sapiens

<400> SEQUENCE: 179

```
tttggagcag gagtgtgatt ctggccaacc accctctctg gcccccaggc gccctcttct       60
tgtggatgtt ctggccaagt gtcaactctg ctctgctgag aagtccaatc caaaggaaga      120
atgccatgtt caacacctac tatgctctag cagtcagtgt ggtgacagcc atctcagggt      180
catccttggc tcaccccaa aggaagatca gcatggtgag cagggcgctg cccttgggca       240
```

<210> SEQ ID NO 180
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180

```
acgttggatg tgtggctggg ctgatctgcg                                        30
```

<210> SEQ ID NO 181
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181

```
acgttggatg ttcagccaaa gcagaggagg                                        30
```

<210> SEQ ID NO 182
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182

```
agttgtctag tttcttaccg gcagg                                             25
```

<210> SEQ ID NO 183
<211> LENGTH: 240
<212> TYPE: DNA
<213> ORGANISM: Homo sapiens

<400> SEQUENCE: 183

```
gtgttctctc tctaccttgc ttcctttacc cacacgctat ttctttgcag acttatgtgc       60
acagtgcggt gttggcagga ggcgtggctg tgggtacctc gtgtcacctg atcccttctc      120
cgtggcttgc catggtgctg ggtcttgtgg ctgggctgat ctccgtcggg ggagccaagt      180
acctgccggt aagaaactag acaactaacc tcctctgctt tggctgaagg ccagcaggac      240
```

<210> SEQ ID NO 184
<211> LENGTH: 240
<212> TYPE: DNA
<213> ORGANISM: Homo sapiens -continued

<400> SEQUENCE: 184

```
gtgttctctc tctaccttgc ttcctttacc cacacgctat ttctttgcag acttatgtgc    60
acagtgcggt gttggcagga ggcgtggctg tgggtacctc gtgtcacctg atcccttctc   120
cgtggcttgc catggtgctg ggtcttgtgg ctgggctgat ctccatcggg ggagccaagt   180
gcctgccggt aagaaactag acaactaatg ctctctgctt tggctgaagg ccagcaggac   240
```

<210> SEQ ID NO 185
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 185

```
tgctgggtct gcttggagag atca                                            24
```

<210> SEQ ID NO 186
<211> LENGTH: 240
<212> TYPE: DNA
<213> ORGANISM: Homo sapiens

<400> SEQUENCE: 186

```
tgccaatctg cttataataa cacttgtcca caggggtgtt gtaaccgagt gctggggatt    60
ccccacagct ccatcatggg ctacaacttc agcttgctgg gtctgcttgg agagatcatc   120
tacattgtgc tgctggtgct tgataccgtc ggagccggca atggcatgtg ggtcactggg   180
cttacccccc atccccttaa cactcccctc caactcagga agaaatgtgt gcagagtcct   240
```

<210> SEQ ID NO 187
<211> LENGTH: 240
<212> TYPE: DNA
<213> ORGANISM: Homo sapiens

<400> SEQUENCE: 187

```
tgccaatctg cttataataa cacttgtcca caggtgtgtt gtaaccgagt gctggggatt    60
caccacatct ccgtcatgca ctccatcttc agcttgctgg gtctgcttgg agagatcacc   120
tacattgtgc tgctggtgct tcatactgtc tggaacggca atggcatgtg ggtcactggg   180
cttacccccc atccccttaa cactcccctc caactcagga agaaatgtgt gcagagtcct   240
```

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 188

```
gtctccaatg ttcgcgcagg cac                                             23
```

<210> SEQ ID NO 189
<211> LENGTH: 240
<212> TYPE: DNA
<213> ORGANISM: Homo sapiens

<400> SEQUENCE: 189

```
agatcaagcc aaaatcagta tgtgggttca tctgcaataa aaatgtttgt tttgctttta    60
cagtttcctc atttggctgt tggattttaa gcaaaagcat ccaagaaaaa caaggcctgt   120
```

```
tcaaaaacaa gacaacttcc tctcactgtt gcctgcattt gtacgtgaga aacgctcatg      180
acagcaaagt ctccaatgtt cgcgcaggca ctggagtcag agaaaatgga gttgaatcct      240
```

<210> SEQ ID NO 190
<211> LENGTH: 232
<212> TYPE: DNA
<213> ORGANISM: Homo sapiens

<400> SEQUENCE: 190

```
agatcaagcc aaaatcagta tgtgggttca tctgcaataa aaatgtttgt tttgcttta       60 cagtttcctc atttggctgt tggattttaa gcaaaagcat ccaagaaaaa caaggcctgt      120
tcaaaaacaa gacaacttcc tctcactgtt gcctgcattt gtacgtgaga aacgctcatg      180
acagcaaagt ctccttatgt ataatgaaac aaggtcagag acagatttga ta             232
```

<210> SEQ ID NO 191
<211> LENGTH: 1960
<212> TYPE: DNA
<213> ORGANISM: Homo sapiens

<400> SEQUENCE: 191

```
tttctaaaag tcaaatgtta gccatcctag aagttgggca taaaatactt gtaagtatat      60
gctaatattc tgatacttaa tgcctgtgaa aaatgtgtat agaattttca attttttaaat    120 agaagtgaag aaaaagcgat aataattact ataaattcaa tatgcagtta tgtatgtatg     180
tgtgtggtta agacaattag gttctcatta agctttgttt ttttaaagat aacatacaca     240
tatattgata atgataaaca attcatatag cttttttgtgt cctctcgttt tgtgacataa    300
aaggtcaatg aaaaaattgg cgattaagtc aaattcgcat ttttcaggac agcagtagag     360
cagtcaggga ggcagatcag cagggcaagt agtcaacgtt actgaattac catgttttgc     420
ttgagaatga atacattgtc agggtactag ggggtaggct ggttgggcgg ggttgagggg     480
gtgttgaggg cggagaaatg caagtttcat tacaaaagtt aacgtaacaa agaatctggt     540
agaagtgagt tttggatagt aaaataagtt tcgaactctg gcaccttcca attttgtcgc     600
actctccttg ttttgacaa tgcaatcata tgcttctgct atgttaagcg tattcaacag      660
cgatgattac agtccagctg tgcaagagaa tattcccgct ctccggagaa gctcttcctt     720
cctttgcact gaaagctgta actctaagta tcagtgtgaa acgggagaaa acagtaaagg     780
caacgtccag gatagagtga agcgacccat gaacgcattc atcgtgtggt ctcgcgatca     840
gaggcgcaag atggctctag agaatcccag aatgcgaaac tcagagatca gcaagcagct     900
gggataccag tggaaaatgc ttactgaagc cgaaaaatgg ccattcttcc aggaggcaca     960
gaaattacag gccatgcaca gagagaaata cccgaattat aagtatcgac tcgtcggaa     1020 ggcgaagatg ctgccgaaga attgcagttt gcttcccgca gatcccgctt cggtactctg    1080
cagcgaagtg caactggaca acaggttgta cagggatgac tgtacgaaag ccacacactc    1140
aagaatggag caccagctag gccacttacc gcccatcaac gcagccagct caccgcagca    1200 acggaccgc tacagccact ggacaaagct gtaggacaat cgggtaacat ggctacaaa     1260 gacctaccta gatgctcctt tttacgataa cttacagccc tcactttctt atgtttagtt    1320
tcaatattgt tttcttttct ctggctaata aaggccttat tcatttcagt tttactggta    1380
tttcatttta aacttaattt caagacaagt tgtgtcaaca cgattaacat gcaaagaaat    1440
aagcatccca gaagtgagcc tgcctatgtt tgtggccgtc agagtactaa cttgataaa     1500 acggacactg tggcttactt taaatgctct aatgagaaac acacttgaaa attgtaccaa    1560
```

-continued

| | |
|---|---|
| aaaaaatcac acttctatat gcagcgtgtt aagcagtcct ctctagaccg tgtattcatt | 1620 |
| ggtctttcag ctactttgta cgtgtctata aattgcaggt aactaaggaa tggatatgta | 1680 |
| agcaggatca aacttgtttc tttctctccc cttcacgctg tggaaaaaac cagttttacc | 1740 |
| tccacttgca attcagttcc tttactccat ataaatccaa acggttgaca tttcctttca | 1800 |
| actagttata aaatgcctct ggtaaaacaa aatatttaat tccttgtcat ttttgtatct | 1860 |
| ctatgaaact tatcattttg cctttcttct gaaaactatc ttttaaaatg gcaatctact | 1920 |
| tgtttccatg gcctattaac ttttaagcct gtggaatgaa | 1960 |

<210> SEQ ID NO 192
<211> LENGTH: 30
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 192
acgttggatg cgcattttc aggacagcag                     30

<210> SEQ ID NO 193
<211> LENGTH: 30
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 193
acgttggatg gtaacgttga ctacttgccc                     30

<210> SEQ ID NO 194
<211> LENGTH: 18
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 194
caggacagca gtagagca                                  18

<210> SEQ ID NO 195
<211> LENGTH: 67
<212> TYPE: DNA
<213> ORGANISM: Homo sapiens

<400> SEQUENCE: 195 cgcattttc aggacagcag tagagcactc agggaggcag atcagcaggg caagtagtca    60
acgttac                                                              67

<210> SEQ ID NO 196
<211> LENGTH: 67
<212> TYPE: DNA
<213> ORGANISM: Homo sapiens

<400> SEQUENCE: 196
gtaacgttga ctacttgccc tgctgatctg cctccctgag tgctctactg ctgtcctgaa    60
aaatgcg                                                              67

<210> SEQ ID NO 197
<211> LENGTH: 30

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
acgttggatg agatggctct agagaatccc                                      30

<210> SEQ ID NO 198
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
acgttggatg gcattttcca ctggtatccc                                      30

<210> SEQ ID NO 199
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
tcccagaatg cgaaactc                                                   18

<210> SEQ ID NO 200
<211> LENGTH: 72
<212> TYPE: DNA
<213> ORGANISM: Homo sapiens

<400> SEQUENCE: 200
agatggctct agagaatccc agaatgcgaa actctgagat cagcaagcag ctgggatacc     60
agtggaaaat gc                                                         72

<210> SEQ ID NO 201
<211> LENGTH: 72
<212> TYPE: DNA
<213> ORGANISM: Homo sapiens

<400> SEQUENCE: 201
gcattttcca ctggtatccc agctgcttgc tgatctcaga gtttcgcatt ctgggattct     60
ctagagccat ct                                                         72

<210> SEQ ID NO 202
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
cgttacccga ttgtcctac                                                  19

<210> SEQ ID NO 203
<211> LENGTH: 80
<212> TYPE: DNA
<213> ORGANISM: Homo sapiens

<400> SEQUENCE: 203

```
agcaacggga ccgctacagc cactggacaa agcagtagga caatcgggta acattggcta    60
caaagaccta cctagatgct                                                80

<210> SEQ ID NO 204
<211> LENGTH: 80
<212> TYPE: DNA
<213> ORGANISM: Homo sapiens

<400> SEQUENCE: 204
agcatctagg taggtctttg tagccaatgt tacccgattg tcctactgct ttgtccagtg    60
gctgtagcgg tcccgttgct                                                80

<210> SEQ ID NO 205
<211> LENGTH: 95
<212> TYPE: DNA
<213> ORGANISM: Homo sapiens

<400> SEQUENCE: 205
tcacgaggtc aggagatcga gacaatcctg gctaacatgg tgaaacccccg tctctactaa   60 aaatacaaca aattcgtagg gccaggtggc aggtg                               95

<210> SEQ ID NO 206
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
acgttggatg aggagatcga gacaatcctg                                     30

<210> SEQ ID NO 207
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
acgttggatg ctggccctac gaatttgttg                                     30

<210> SEQ ID NO 208
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
cggccctacg aatttgttgt attttt                                         26

<210> SEQ ID NO 209
<211> LENGTH: 81
<212> TYPE: DNA
<213> ORGANISM: Homo sapiens

<400> SEQUENCE: 209
gctacttctc taccttatgg cagggacttg tcgctaggca atggtggcat tcattgtgat    60
gctagccaga gctcacagct c                                              81
```

```
<210> SEQ ID NO 210
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
acgttggatg taccttatgg cagggacttg                                        30

<210> SEQ ID NO 211
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
acgttggatg ctctggctag catcacaatg                                        30

<210> SEQ ID NO 212
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
gggacttgtc gctagg                                                       16

<210> SEQ ID NO 213
<211> LENGTH: 212
<212> TYPE: DNA
<213> ORGANISM: Homo sapiens

<400> SEQUENCE: 213
acctcatcct gggcaccctg gttatatcaa cttcagctat gaggtaattt ttctctttac       60 taatttgac cattgtttgc gttaacaatg ccctgggctc tgtaaagaat agtgtgttga      120
ttctttatcc cagatgtttc tcaagtggtc ctgattttac agttcctacc accagcttcc     180
cagtttaagc tctgatggtt ggcctcaagc ct                                   212

<210> SEQ ID NO 214
<211> LENGTH: 218
<212> TYPE: DNA
<213> ORGANISM: Homo sapiens

<400> SEQUENCE: 214
acctcatcct gggcaccctg gttatatcaa cttcagctat gaggtaattt ttctctttac       60 taatttgat cactgtttgc attagcagtc ccctgggctc tgtaaagaat agtgggtgga      120
ttcttcatcc caaataaagt ggtttctcaa gtggtcccaa ttttacagtt cctaccatca     180
gcttcccagt ttaagctctg atggttggcc tcaagcct                             218

<210> SEQ ID NO 215
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 215
acgttggatg ccctgggctc tgtaaagaat                                       30

<210> SEQ ID NO 216
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
acgttggatg aggcttgagg ccaaccatca g                                     31

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
ttcttcatcc caaataaagt                                                  20

<210> SEQ ID NO 218
<211> LENGTH: 122
<212> TYPE: DNA
<213> ORGANISM: Homo sapiens

<400> SEQUENCE: 218
ccctgggctc tgtaaagaat agtgtgttga ttctttatcc cagaagtttc tcaagtggtc      60
ctgattttac agttcctacc accagcttcc cagtttaagc tctgatggtt ggcctcaagc     120
ct                                                                   122

<210> SEQ ID NO 219
<211> LENGTH: 122
<212> TYPE: DNA
<213> ORGANISM: Homo sapiens

<400> SEQUENCE: 219
aggcttgagg ccaaccatca gagcttaaac tgggaagctg gtggtaggaa ctgtaaaatc      60
aggaccactt gagaaacttc tgggataaag aatcaacaca ctattcttta cagagcccag     120
gg                                                                   122

<210> SEQ ID NO 220
<211> LENGTH: 128
<212> TYPE: DNA
<213> ORGANISM: Homo sapiens

<400> SEQUENCE: 220
ccctgggctc tgtaaagaat agtgggtgga ttcttcatcc caaataaagt cgtttctcaa      60
gtggtcccaa ttttacagtt cctaccatca gcttcccagt ttaagctctg atggttggcc     120
tcaagcct                                                             128

<210> SEQ ID NO 221
<211> LENGTH: 128
<212> TYPE: DNA
<213> ORGANISM: Homo sapiens

<400> SEQUENCE: 221
```

-continued

```
aggcttgagg ccaaccatca gagcttaaac tgggaagctg atggtaggaa ctgtaaaatt    60
gggaccactt gagaaacgac tttatttggg atgaagaatc cacccactat tctttacaga   120
gcccaggg                                                            128
```

<210> SEQ ID NO 222
<211> LENGTH: 30
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 222

```
acgttggatg tatcaacttc agctatgagg                                     30
```

<210> SEQ ID NO 223
<211> LENGTH: 28
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 223

```
acgttggatg cactattctt tacagagc                                       28
```

<210> SEQ ID NO 224
<211> LENGTH: 17
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 224

```
ctttacagag cccaggg                                                   17
```

<210> SEQ ID NO 225
<211> LENGTH: 90
<212> TYPE: DNA
<213> ORGANISM: Homo sapiens

<400> SEQUENCE: 225

```
tatcaacttc agctatgagg taattttct ctttactaat tttgaycayt gtttgcrtta     60
rcartaccct gggctctgta aagaatagtg                                     90
```

<210> SEQ ID NO 226
<211> LENGTH: 90
<212> TYPE: DNA
<213> ORGANISM: Homo sapiens

<400> SEQUENCE: 226

```
cactattctt tacagagccc agggtartgr taargcaaac aytgytcaaa attagtaaag    60
agaaaaatta cctcatagct gaagttgata                                     90
```

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 227

```
ccctgggctc tgtaaagaat                                               20

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
gagcttaaac tgggaagctg                                               20

<210> SEQ ID NO 229
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
ccctgggctc tgtaaagaat agt                                           23

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
ttcttcatcc caaataaagt g                                             21

<210> SEQ ID NO 231
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
ccctgggctc tgtaaagaat agtg                                          24

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
ctgggctctg taaagaatag t                                             21

<210> SEQ ID NO 233
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
ctgggctctg taaagaatag tg                                            22
```

<210> SEQ ID NO 234
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
caggacagca gtagagcag                                              19

<210> SEQ ID NO 235
<211> LENGTH: 68
<212> TYPE: DNA
<213> ORGANISM: Homo sapiens

<400> SEQUENCE: 235
gctcagtatc ttcagcagtg tccatttgaa gatcatgtaa aattagtgaa tgaagtaact    60
gaatttgc                                                            68

<210> SEQ ID NO 236
<211> LENGTH: 68
<212> TYPE: DNA
<213> ORGANISM: Homo sapiens

<400> SEQUENCE: 236
gctcagtatc ttcagcagtg tccatttgaa gatcatgtaa aattagtgaa tgaagtaact    60
gaatttgc                                                            68

<210> SEQ ID NO 237
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
acgttggatg cagtatcttc agcagtgtcc                                   30

<210> SEQ ID NO 238
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
acgttggatg gcaaattcag ttacttcatt c                                 31

<210> SEQ ID NO 239
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
cagtgtccat ttgaagatc                                               19

<210> SEQ ID NO 240
<211> LENGTH: 65
<212> TYPE: DNA

-continued

```
<213> ORGANISM: Homo sapiens

<400> SEQUENCE: 240
cagtatcttc agcagtgtcc atttgaagat cttgtaaaat tagtgaatga agtaactgaa    60
tttgc                                                                65

<210> SEQ ID NO 241
<211> LENGTH: 65
<212> TYPE: DNA
<213> ORGANISM: Homo sapiens

<400> SEQUENCE: 241
gcaaattcag ttacttcatt cactaatttt acaagatctt caaatggaca ctgctgaaga    60
tactg                                                                65
```